United States Patent
Yokoyama et al.

(10) Patent No.: US 12,076,087 B2
(45) Date of Patent: Sep. 3, 2024

(54) INFORMATION PROCESSING APPARATUS AND INFORMATION PROCESSING METHOD

(71) Applicant: SONY CORPORATION, Tokyo (JP)

(72) Inventors: Masayuki Yokoyama, Tokyo (JP); Takuro Noda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 895 days.

(21) Appl. No.: 17/040,042

(22) PCT Filed: Feb. 20, 2019

(86) PCT No.: PCT/JP2019/006216
§ 371 (c)(1),
(2) Date: Sep. 21, 2020

(87) PCT Pub. No.: WO2019/187808
PCT Pub. Date: Oct. 3, 2019

(65) Prior Publication Data
US 2021/0019493 A1 Jan. 21, 2021

(30) Foreign Application Priority Data

Mar. 29, 2018 (JP) ................................. 2018-063486

(51) Int. Cl.
*A61B 3/113* (2006.01)
*A61B 3/00* (2006.01)
(Continued)

(52) U.S. Cl.
CPC ............. *A61B 3/113* (2013.01); *A61B 3/0008* (2013.01); *A61B 3/14* (2013.01); *A61B 5/7221* (2013.01);
(Continued)

(58) Field of Classification Search
CPC ......... A61B 3/113; A61B 3/0008; A61B 3/14; A61B 5/7221; G06T 7/70; G06T 7/73;
(Continued)

(56) References Cited

U.S. PATENT DOCUMENTS

2006/0210122 A1 9/2006 Cleveland et al.
2011/0249868 A1* 10/2011 Tsukizawa ............. A61B 5/163
382/103
(Continued)

FOREIGN PATENT DOCUMENTS

JP 2001-061785 A 3/2001
WO 99/005988 A2 2/1999
(Continued)

OTHER PUBLICATIONS

Setiawan et al, Determine Focus Based on Eye Gazing Direction, 2017, 3rd International Conference on Science in Information Technology, pp. 1-5. (Year: 2017).*
(Continued)

*Primary Examiner* — Aaron W Carter
*Assistant Examiner* — Kathleen M Broughton
(74) *Attorney, Agent, or Firm* — CHIP LAW GROUP

(57) ABSTRACT

An information processing apparatus according to an embodiment of the present technology includes an acquisition section and a processor. The acquisition section acquires eye information regarding an eye of a user. The processor determines a first line-of-sight direction on the basis of the eye information using a first method, determines a second line-of-sight direction on the basis of the eye information using a second method that is different from the first method, calculates reliability information regarding at least one of reliability of the first line-of-sight direction or reliability of
(Continued)

the second line-of-sight direction, and determines a line-of-sight direction of the user on the calculated reliability information.

15 Claims, 14 Drawing Sheets

(51) Int. Cl.
| | |
|---|---|
| *A61B 3/14* | (2006.01) |
| *A61B 5/00* | (2006.01) |
| *G06T 7/70* | (2017.01) |
| *G06V 10/80* | (2022.01) |
| *G06V 40/16* | (2022.01) |
| *G06V 40/19* | (2022.01) |
| *G06V 40/18* | (2022.01) |

(52) U.S. Cl.
CPC .............. *G06T 7/70* (2017.01); *G06V 10/809* (2022.01); *G06V 40/171* (2022.01); *G06V 40/19* (2022.01); *G06T 2207/30201* (2013.01); *G06V 40/193* (2022.01)

(58) Field of Classification Search
CPC . G06T 2207/30201; G06T 2207/10152; G06T 2207/30041; G06T 2207/30204; G06V 10/809; G06V 40/171; G06V 40/19; G06V 40/193; G06F 18/254; G02B 2027/0178; G02B 27/0093; G02B 27/0172
See application file for complete search history.

(56) References Cited

U.S. PATENT DOCUMENTS

| | | | | |
|---|---|---|---|---|
| 2012/0189160 | A1* | 7/2012 | Kaneda | G06V 40/19 348/207.99 |
| 2014/0028977 | A1* | 1/2014 | Umekawa | A61B 3/152 351/208 |
| 2015/0293381 | A1* | 10/2015 | Mizuno | G02C 13/005 351/159.75 |
| 2016/0004303 | A1* | 1/2016 | Arar | G06F 3/013 345/156 |
| 2016/0063304 | A1* | 3/2016 | Yamashita | G06V 10/143 348/78 |
| 2017/0293354 | A1* | 10/2017 | Lu | G06V 20/64 |

FOREIGN PATENT DOCUMENTS

| | | |
|---|---|---|
| WO | 2006/101943 A2 | 9/2006 |
| WO | 2016/098406 A1 | 6/2016 |

OTHER PUBLICATIONS

International Search Report and Written Opinion of PCT Application No. PCT/JP2019/006216, issued on May 7, 2019, 09 pages of ISRWO.

* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2019/006216 filed on Feb. 20, 2019, which claims priority benefit of Japanese Patent Application No. JP 2018-063486 filed in the Japan Patent Office on Mar. 29, 2018. Each of the above-referenced applications is hereby incorporated herein by reference in its entirety.

TECHNICAL FIELD

The present technology relates to an information processing apparatus, an information processing method, and a program that are applicable to detection of a line-of-sight direction of a user.

BACKGROUND ART

Conventionally, a technology is known that detects a line-of-sight direction of a user. For example, it is possible to detect a point at which a user is gazing, a state of the user, and the like using a line-of-sight direction of the user.

Patent Literature 1 discloses an eyewear terminal used to detect a line of sight of a user. In Patent Literature 1, a line of sight of a user is detected using a pupil-corneal reflection method. The eyewear terminal is equipped with a light source that emits infrared light and an imaging unit that captures an image of an eyeball. Infrared light is irradiated onto an eyeball by the light source, and an image of the eyeball in which a bright spot (a Purkinje image) of the infrared light is reflected is captured by the imaging unit. The line of sight of the user is estimated on the basis of, for example, positions of the bright spot and a pupils (for example, paragraphs [0014], [0015], [0021], [0022], and [0048] of the specification, and FIGS. 2 and 7 in Patent Literature 1).

CITATION LIST

Patent Literature

Patent Literature 1: WO2016/098406

DISCLOSURE OF INVENTION

Technical Problem

A technology that detects a line-of-sight direction of a user is expected to be applied in various fields such as fields of amusement, traffic, medical care, marketing, and the like, and there is a demand for a technology that stably detects a line of sight.

In view of the circumstances described above, it is an object of the present technology to provide an information processing apparatus, an information processing method, and a program that make it possible to stably detect a line of sight.

Solution to Problem

In order to achieve the object described above, an information processing apparatus according to an embodiment of the present technology includes an acquisition section and a processor.

The acquisition section acquires eye information regarding an eye of a user.

The processor determines a first line-of-sight direction on the basis of the eye information using a first method, determines a second line-of-sight direction on the basis of the eye information using a second method that is different from the first method, calculates reliability information regarding at least one of reliability of the first line-of-sight direction or reliability of the second line-of-sight direction, and determines a line-of-sight direction of the user on the calculated reliability information.

In the information processing apparatus, eye information regarding an eye of a user is acquired, and a first line-of-sight direction and a second line-of-sight direction are respectively determined on the basis of the eye information regarding the eye of the user, using a first method and a second method that are different from each other. Further, reliability information regarding at least one of reliability of the first line-of-sight direction or reliability of the second line-of-sight direction is calculated, and a line-of-sight direction of the user is determined on the basis of the reliability information. This makes it possible to stably detect a line of sight.

On the basis of the reliability information, the processor may synthesize the first line-of-sight direction and the second line-of-sight direction, and may determine the line-of-sight direction of the user.

It is possible to make, for example, a result of detecting a line of sight stable by synthesizing line-of-sights respectively determined using different methods. This makes it possible to stably detect a line of sight.

The reliability information may include a weighting coefficient used to synthesize the first line-of-sight direction and the second line-of-sight direction.

This makes it possible to perform synthesis according to, for example, the reliability of each line-of-sight direction, and thus to improve the reliability. This results in being able to stably detect a line of sight with a high degree of reliability.

The eye information may include an eyeball image of an eyeball of the user, the eyeball image being obtained by performing image-capturing on the eyeball in a state of being irradiated with at least one piece of irradiation light. In this case, the first method may be a method including detecting, from the eyeball image, at least one bright spot generated due to the at least one piece of irradiation light, and determining the first line-of-sight direction on the basis of the detected at least one bright spot.

This makes it possible to determine a line-of-sight direction on the basis of a bright spot generated due to irradiation light, and thus to improve the accuracy in detecting a line-of-sight direction.

The at least one piece of irradiation light may be a plurality of pieces of irradiation light. In this case, the processor may be capable of detecting, from the eyeball image, a pair of bright spots from among a plurality of bright spots generated due to the plurality of pieces of irradiation light, the pair of bright spots being a pair of bright spots provided in a specified arrangement.

This makes it possible to detect a line of sight using, for example, an eyeball model. This results in being able to detect a line of sight of a user with a sufficiently high degree of accuracy.

The processor may detect a corneal region of the eyeball, and may calculate the weighting coefficient on the basis of a position of the pair of bright spots in the corneal region.

This makes it possible to, for example, properly calculate the reliability of a line-of-sight direction detected using a bright spot, and to properly calculate a weighting coefficient and the like.

The processor may detect a pupil center of the eyeball, and may calculate the weighting coefficient on the basis of a distance from the pair of bright spots to the pupil center.

This makes it possible to, for example, accurately calculate the reliability of a line-of-sight direction detected using a bright spot, and to calculate a weighting coefficient and the like with a high degree of accuracy.

The processor may calculate an area of the bright spot, and calculates the weighting coefficient on the basis of the calculated area of the bright spot.

This makes it possible to, for example, calculate a weighting coefficient according to a state of a bright spot, and to perform, for example, synthesis of a line-of-sight direction with a high degree of accuracy.

The first method may be a method of determining the first line-of-sight direction on the basis of the pair of bright spots from among the plurality of bright spots. In this case, the second method may be a method of determining the second line-of-sight direction on the basis of a single bright spot from among the plurality of bright spots.

Consequently, even when a pair of bright spots is not detected, it is possible to detect a line-of-sight direction, and to perform a highly stable line-of-sight detection.

The processor may update at least one of a first correction parameter or a second correction parameter on the basis of the reliability information, the first correction parameter being used to determine the first line-of-sight direction, the second correction parameter being used to determine the second line-of-sight direction.

This makes it possible to maintain a correction parameter in a newest state, and to stably detect a line of sight.

The first method may be a method of determining the first line-of-sight direction on the basis of a reference point that is set on a surface of the eyeball. The processor may update the second correction parameter on the basis of the first line-of-sight direction.

For example, the use of a reference point makes it possible to accurately detect a line-of-sight direction even when there is a positional shift of the apparatus, or the like. Consequently, it is possible to properly correct a correction parameter of the other method.

The reliability information may include reliability of the first line-of-sight direction. In this case, the processor may update the second correction parameter according to the reliability of the first line-of-sight direction.

This makes it possible to properly correct a correction parameter of one of the methods using the reliability of the other method as a reference.

The eye information may include an eyeball image of an eyeball of the user, the eyeball image being obtained by performing image-capturing on the eyeball in a state of being irradiated with at least one piece of irradiation light. In this case, the first method may be a method including detecting, from the eyeball image, at least one bright spot generated due to the at least one piece of irradiation light, and determining the first line-of-sight direction on the basis of the detected at least one bright spot. Further, the processor may calculate the reliability of the first line-of-sight direction on the basis of the eyeball image.

This makes it possible to accurately calculate the first line-of-sight direction. This results in being able to accurately update the second correction parameter, and to stably detect a line of sight.

The at least one piece of irradiation light may be irradiated onto one of a central region or a surrounding region of the eye region.

This makes it possible to, for example, stably detect a line-of-sight direction of a user in a wide range of the field of view.

The processor may update the second correction parameter according to a position of a pupil in an eye region in the eyeball image, the eye region including the eyeball.

This makes it possible to, for example, update the second correction parameter at a position in which the first line-of-sight direction is accurately calculated, and to improve the accuracy in update processing.

The reliability information may include a weighting coefficient used to synthesize the first line-of-sight direction and the second line-of-sight direction. In this case, the processor may correct the second correction parameter on the basis of the weighting coefficient.

This makes it possible to accurately update the second correction parameter, and to perform a sufficiently stable line-of-sight detection.

The second method may be a method of determining the second line-of-sight direction by detecting at least one of a position or a shape of a specified feature of the eyeball from the eyeball image.

This makes it possible to, for example, detect a field-of-view direction of the user over a wide range of the field of view. This results in being able to broaden a range in which a line-of-sight direction is detectable.

The specified feature may include one of a pupil, a cornea, and an iris of the eyeball.

This makes it possible to easily detect a line-of-sight direction.

An information processing method according to an embodiment of the present technology is performed by a computer system, and includes acquiring eye information regarding an eye of a user.

A first line-of-sight direction is determined on the basis of the eye information using a first method, a second line-of-sight direction is determined on the basis of the eye information using a second method that is different from the first method, reliability information regarding at least one of reliability of the first line-of-sight direction or reliability of the second line-of-sight direction is calculated, and a line-of-sight direction of the user is determined on the basis of the calculated reliability information.

A program according to an embodiment of the present technology causes a computer system to perform a process including:

acquiring eye information regarding an eye of a user;
determining a first line-of-sight direction on the basis of the eye information using a first method;
determining a second line-of-sight direction on the basis of the eye information using a second method that is different from the first method;
calculating reliability information regarding at least one of reliability of the first line-of-sight direction or reliability of the second line-of-sight direction; and
determining a line-of-sight direction of the user on the basis of the calculated reliability information.

Advantageous Effects of Invention

As described above, the present technology makes it possible to stably detect a line of sight. Note that the effect described here is not necessarily limitative, and any of the effects described in the present disclosure may be provided.

MODE(S) FOR CARRYING OUT THE INVENTION

Embodiments according to the present technology will now be described below with reference to the drawings.

First Embodiment

Figure 1:
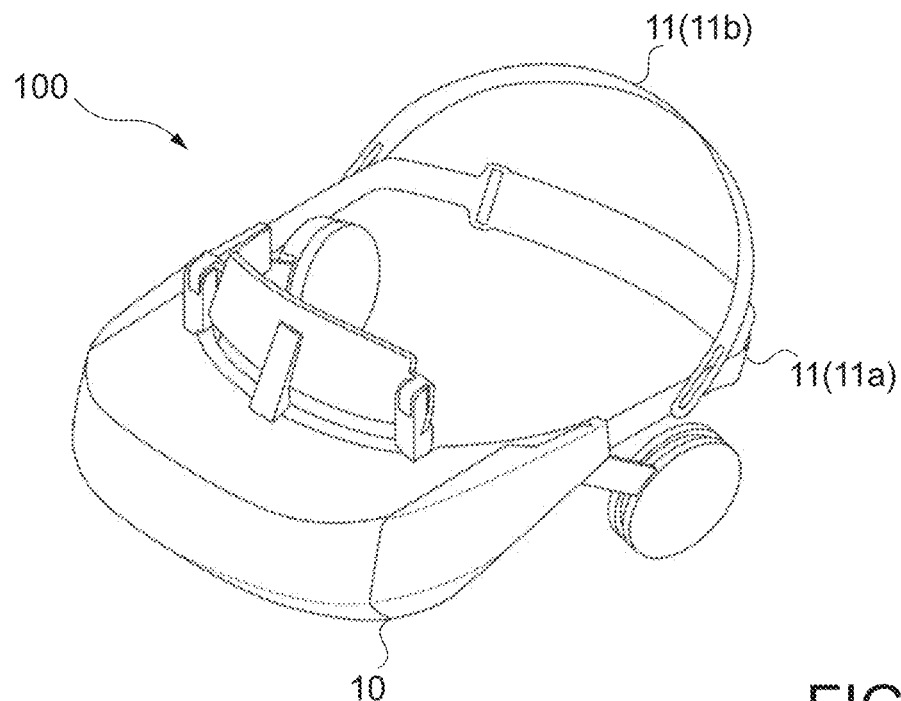
FIG. 1 is a perspective view illustrating an appearance of a head-mounted display (HMD) according to a first embodiment of the present technology.
Figure 2:
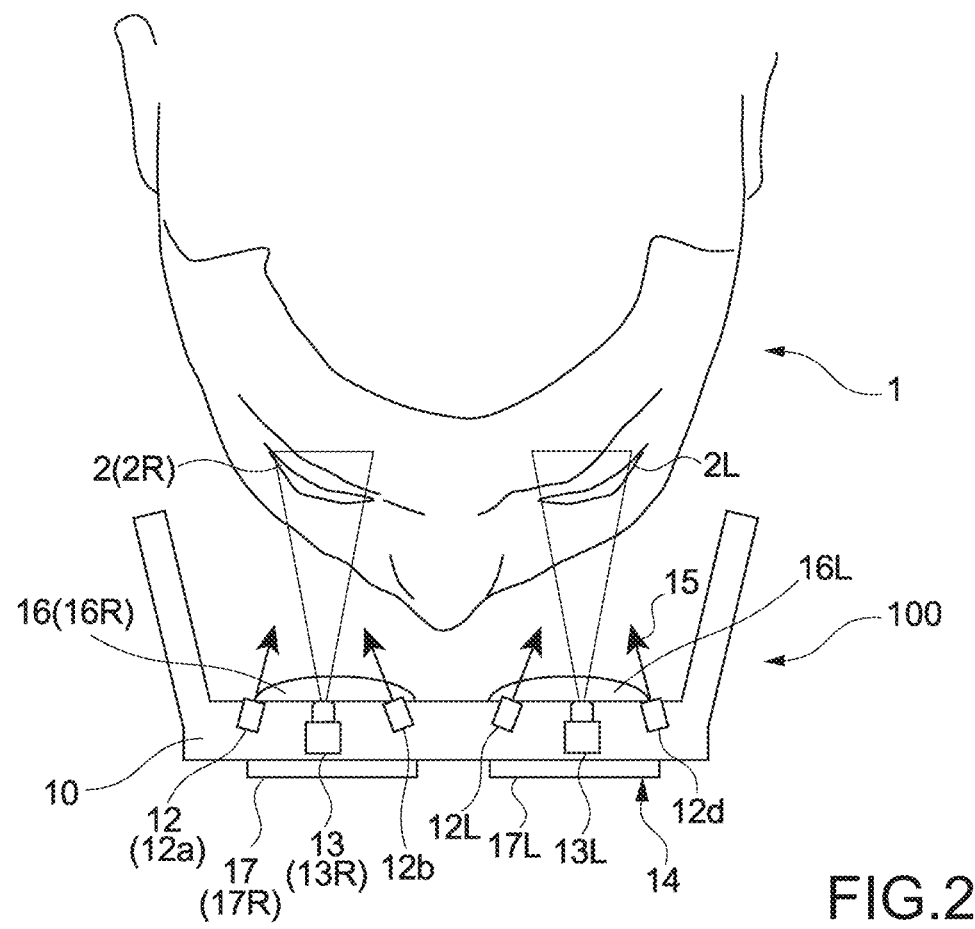
FIG. 2 schematically illustrates an example of a configuration of the HMD.

FIG. 1 is a perspective view illustrating an appearance of a head-mounted display (the HMD) according to a first embodiment of the present technology. FIG. 2 schematically illustrates an example of a configuration of an HMD 100. FIG. 2 schematically illustrates the example of the configuration of the HMD 100 when a user 1 who is wearing the HMD 100 is viewed from above.

The HMD 100 includes a base 10, an attachment band 11, an infrared light source 12, an infrared camera 13, and a display unit 14. The HMD 100 is used by being worn on the head of the user 1, and serves as a display apparatus that displays thereon an image in the field of view of the user 1.

The base 10 is a member arranged in front of right and left eyes 2 (2L and 2R) of the user 1. The base 10 is configured to cover the field of view of the user 1, and serves as a housing that accommodates, for example, the display unit 14 used to display an image.

The attachment band 11 is attached to the head of the user 1. As illustrated in FIG. 1, the attachment band 11 includes a side-of-head band 11a and a top-of-head band 11b. The side-of-head band 11a is connected to the base 10, and is attached to surround the head of the user from the side to the back of the head. The top-of-head band 11b is connected to the side-of-head band 11a, and is attached to surround the head of the user from the side to the top of the head. This makes it possible to hold the base 10 in front of the eyes of the user 1.

The infrared light source 12 emits infrared light 15 to the eye 2 of the user 1. The infrared light source 12 is provided to the base 10 to face the eye 2 of the user 1. In the present embodiment, a plurality of infrared light sources 12 is used. FIG. 2 schematically illustrates four infrared light sources 12a to 12d arranged on the base 10. The infrared light sources 12a and 12b irradiate the infrared light 15 onto the right eye 2R of the user 1, and the infrared light sources 12c and 12d irradiate the infrared light 15 onto the left eye 2L of the user 1. In the present embodiment, the infrared light 15 corresponds to illumination light.

In the present embodiment, the respective infrared light sources 12 are arranged such that the infrared light 15 is irradiated onto a central region in an eye region of the user 1. In the present disclosure, the eye region is a region in which the eyeball of the user 1 is visible when the user 1 opens his/her eyes. In other words, the eye region is a region between upper and lower eyelids in which a non-white part of the eyeball (such as a pupil, a cornea, and an iris) and a white part of the eyeball (such as a sclera) are visible. Thus, for example, the central region of an eye region is a region in which there exists a non-white part of the eyeball when the user 1 is looking at the front.

A light-emitting device, such as an infrared (IR)-light emitting diode (LED) or an IR-laser diode (LD), that is capable of emitting an infrared ray is used as the infrared light source 12. The specific configuration of the infrared light source 12 is not limited, and, for example, any light source that is capable of emitting an infrared ray may be used as the infrared light source. Further, the number of infrared light sources 12, the arrangement of the infrared light source 12, and the like may be set as appropriate such that, for example, it is possible to perform a line-of-sight detection and the like with a desired degree of accuracy. In the present embodiment, the infrared light 15 corresponds to irradiation light.

The infrared camera 13 is a camera that detects infrared light coming from a target to capture an image of the target. The infrared camera 13 includes, for example, a filter (an IR filter) that absorbs visible light and through which an infrared ray is transmitted. This results in detecting reflected light or the like of an infrared wavelength that comes from a target irradiated with the infrared light 15. A digital camera that includes, for example, an image sensor such as a complementary metal-oxide semiconductor (CMOS) sensor or a charge coupled device (CCD) sensor is used as the infrared camera 13.

In the present embodiment, an infrared camera 13L and an infrared camera 13R that respectively capture an image of the left eye 2L of the user 1 and an image of the right eye 2R of the user 1 are used. The infrared cameras 13L and 13R are respectively installed at specified positions in the HMD 100, specifically, at specified positions in the base 10 to be respectively oriented toward the left eye 2L and the right eye 2R of the user 1. Thus, the relative positions of the infrared camera 13L and the infrared camera 13R with respect to the eyes 2 of the user 1 are changed as the relative position of the base 10 with respect to the eyes 2 of the user 1 is changed. Note that FIG. 2 schematically illustrates, image-capturing ranges of the respective infrared cameras 13L and 13R.

Figure 3:
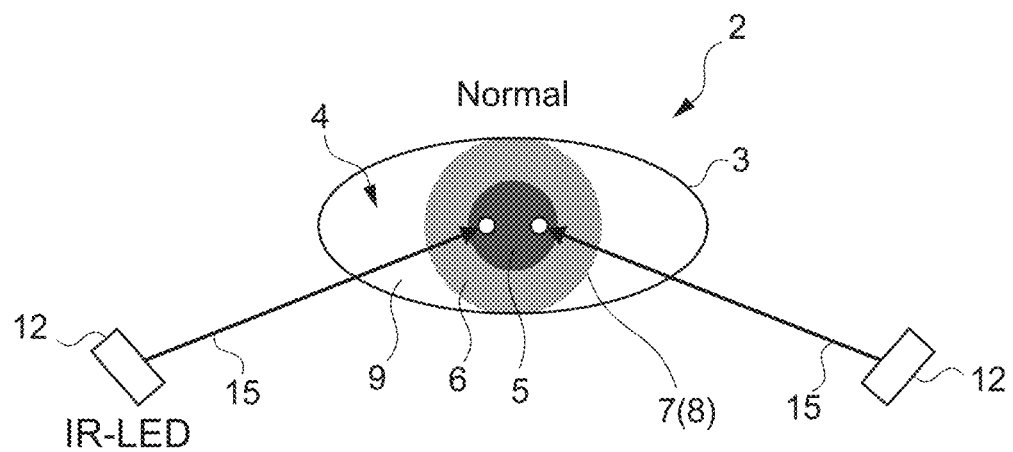
FIG. 3 is a schematic diagram for describing a state of an eye of a user that is irradiated with infrared light.
Figure 4:
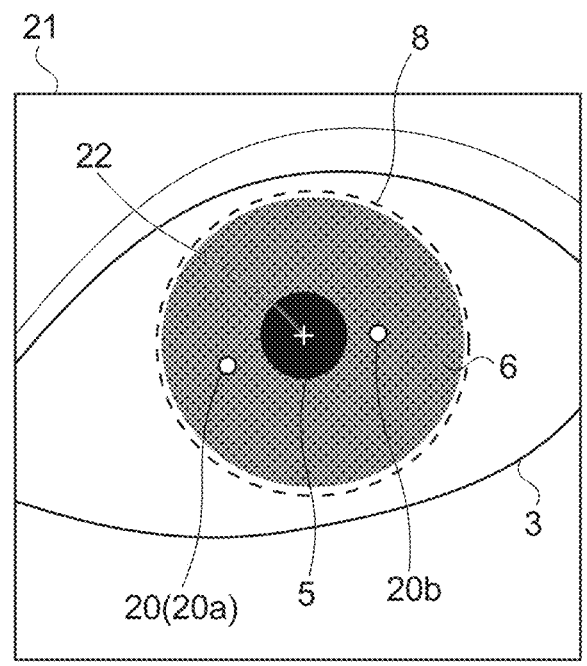
FIG. 4 schematically illustrates an example of an image captured by an infrared camera.

FIG. 3 is a schematic diagram for describing a state of the eye 2 of the user 1 that is irradiated with the infrared light 15. FIG. 4 schematically illustrates an example of an image captured by the infrared camera 13. FIG. 3 schematically illustrates the eye 2 of the user 1 (an eye region 3) when the user 1 is looking at the front. The eye region 3 includes an eyeball 4 of the user 1. A black circular region in the center of the eye region 3 is a pupil 5, and a gray annular region surrounding the pupil 5 is an iris 6. There exists a transparent cornea 7 in a range including the pupil 5 and the iris 6.

Note that the range (a corneal region 8) in which there exists the cornea 7 is a range having substantially the same size as the iris 6. Thus, a region that includes the iris 6 and the pupil 5 is the corneal region 8. Further, for example, a region that is not a region of a white part of the eyeball (a sclera 9) that is situated outside of the iris 6, that is, a region of a non-white part of the eyeball can also be considered the corneal region 8. A point on each of the iris 6 and the pupil 5 may be hereinafter referred to as a point on the cornea (a point in the corneal region 8).

As illustrated in FIG. 3, the infrared light 15 emitted from the infrared light source 12 is reflected off the eyeball 4 of the user 1. At this point, a bright spot 20 is generated at an incident point (a reflection point) of the infrared light 15 since the intensity of the reflected light is high. It is possible to capture an image of the bright spot 20 of the reflected light (a Purkinje image) using the infrared camera 13.

In present embodiment, as described above, the infrared light 15 is irradiated onto the vicinity of the center of the eye region 3. Thus, when, for example, the user 1 is looking at the front, the infrared light 15 is irradiated onto the corneal region 8 (a region on the pupil 5 in the example illustrated in FIG. 3), and this results in the bright spot 20 being generated in the corneal region 8. Note that, when a line of sight of the user 1 is moved, the bright spot 20 may be generated outside of the corneal region 8. Further, when the relative position of the eyes of the user 1 with respect to the HMD 100 is shifted, there may be a change in a position at which the bright spot 20 is generated.

For example, the infrared cameras 13L and 13R respectively capture an image of the left eye 2L of the user 1 and an image of the right eye 2R of the user 1 in a state in which the left eye 2L and the right eye 2R of the user 1 are irradiated with the infrared light 15. Accordingly, image data making up an infrared image of the left eyeball 4 is output from the infrared camera 13L, and image data making up an infrared image of the right eyeball 4 is output from the infrared camera 13R. An infrared image captured by the infrared camera 13 is hereinafter referred to as an eyeball image 21.

As described above, the eyeball image 21 of the eyeball 4 that is obtained by performing image-capturing on the eyeball 4 in a state of being irradiated with the infrared light is an image of the bright spot 20. For example, as illustrated in FIG. 4, the bright spot 20 having a higher intensity than that of the surroundings is reflected in a position that the infrared light 15 has entered. FIG. 4 schematically illustrates bright spots 20a and 20b that are generated by the pieces of infrared light 15 respectively irradiated by two infrared light sources 12. For example, when a plurality of infrared light sources 12 is used, the number of bright spots 20 generated is the same as the number of infrared light sources 12. Note that a pseudo-bright spot or the like may be generated that is generated by the infrared light 15 being reflected off another portion of the eye 2 of the user 1.

Returning to FIG. 2, the display unit 14 includes a lens system 16 and a display 17. The lens system 16 includes a left-eye lens 16L arranged in front of the left-eye 2L and a right-eye lens 16R arranged in front of the right-eye 2R. Any configuration may be adopted for the lens system 16 of each of the left-eye 2L and the right-eye 2R. The configuration of the lens system 16 is not limited to a case in which a single lens is arranged, and a plurality of arbitrary optical members such as various lenses such as a Fresnel lens and an optical filter may be arranged.

The display 17 is provided to the base 10 to cover at least a portion of the field of view of the user 1. In the present embodiment, a display 17L that displays thereon an image for the left eye 2L, and a display 17R for displays thereon an image for the right eye 2R are used. The display 17L is arranged on the other side of the left eye lens 16L with respect to the left eye 2. The display 17R is arranged on the other side of the right eye 2R with respect to the right eye lens 16R.

For example, an organic EL display, a liquid crystal display (LCD), or the like is used as the display 17. The specific configuration of the display 17 is not limited. For example, a single display 17 may be used to display an image for the left-eye 2L and an image for the right-eye 2R.

In the following description, the left eye 2L and the right eye 2R of the user 1 may both be simply referred to as an eye of the user 1 without distinguishing from each other. Further, in the following description, the infrared camera 13L and the infrared camera 13R may both be referred to as the infrared camera 13, the left-eye lens 16L and the right-eye lens 16R may both be referred to as a lens 16, and the display 17L and the display 17R may both be referred to as the display 17.

Figure 5:
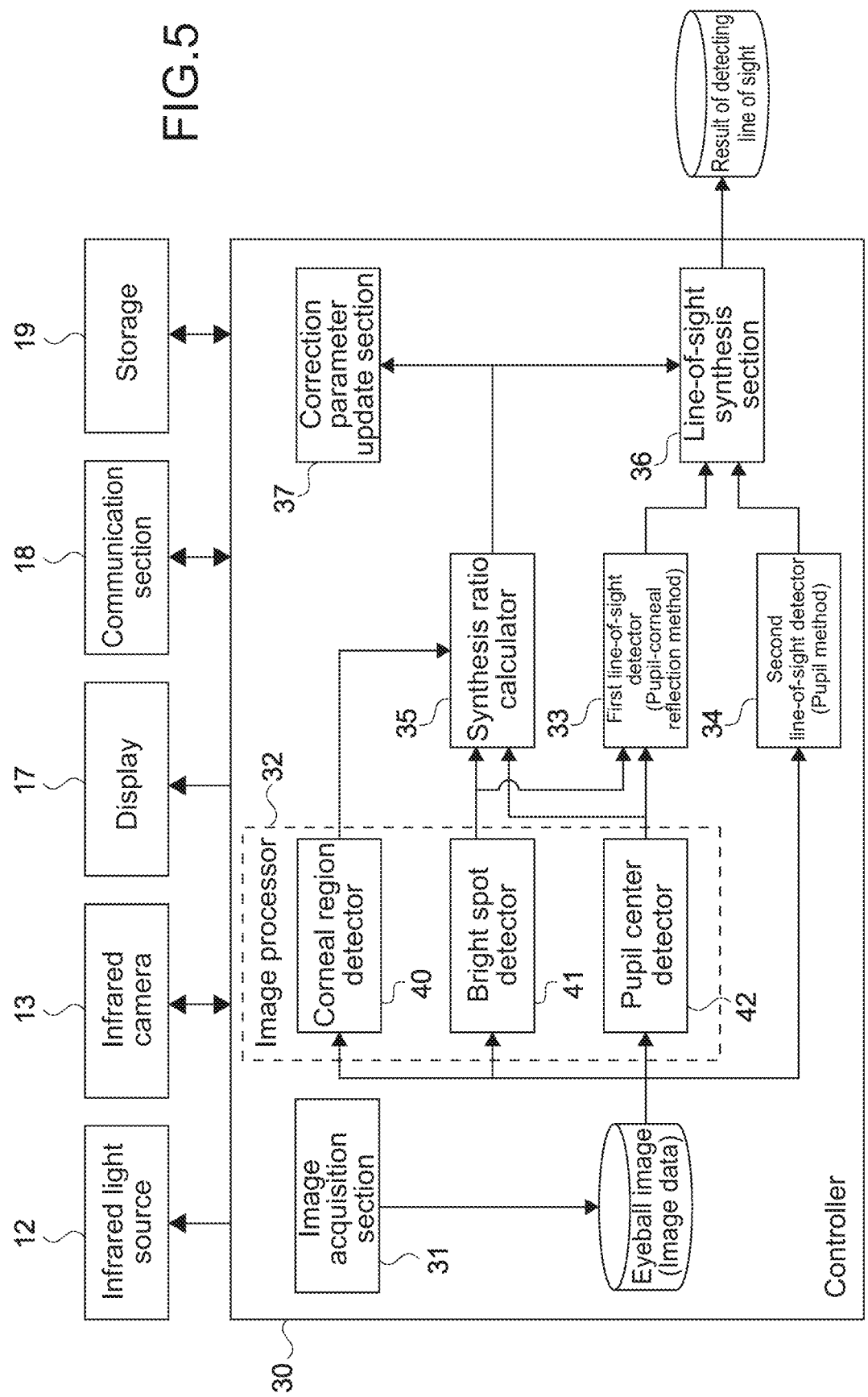
FIG. 5 is a block diagram illustrating an example of a functional configuration of the HMD.

FIG. 5 is a block diagram illustrating an example of a functional configuration of the HMD 100. The HMD 100 further includes a communication section 18, a storage 19, and a controller 30.

The communication section 18 is a module used to perform network communication, Near-field communication, or the like with other devices. For example, a wireless LAN module such as Wi-Fi, or a communication module such as Bluetooth (registered trademark) is provided.

The storage 19 is a nonvolatile storage device, and, for example, a solid state drive (SSD), a hard disk drive (HDD), or the like is used. The storage 19 stores therein a control program used to control an operation of the overall HMD 100. Further, the storage 19 stores therein a correction parameter. The correction parameter is a parameter used when detecting a line-of-sight direction of the user 1. The correction parameter will be described later in detail. In addition, various data, various programs, and the like that are necessary for the operation of the HMD 100 are stored in the storage 19 as appropriate. The method of installing the control program or the like on the HMD 100 is not limited.

The controller 30 controls operations of the respective blocks of the HMD 100. The controller 30 is configured by hardware, such as a CPU and a memory (a RAM and a ROM), that is necessary for a computer. Various processes are performed by the CPU loading, into the RAM, the control program stored in the storage 19 and executing the control program. In the present embodiment, the controller 30 corresponds to an information processing apparatus.

For example, a programmable logic device (PLD) such as a field programmable gate array (FPGA), or other devices such as an application specific integrated circuit (ASIC) may be used as the controller 30.

In the present embodiment, an image acquisition section 31, an image processor 32, a first line-of-sight detector 33, a second line-of-sight detector 34, a synthesis ratio calculator 35, a line-of-sight synthesis section 36, and a correction parameter update section 37 are implemented as functional blocks by the CPU of the controller 30 executing the program according to the present embodiment. Then, the information processing method according to the present embodiment is performed by these functional blocks. In order to implement each functional block, dedicated hardware such as an integrated circuit (IC) may be used as appropriate. In the present embodiment, the image processor 32, the first line-of-sight detector 33, the second line-of-sight detector 34, the synthesis ratio calculator 35, the line-of-sight synthesis section 36, and the correction parameter update section 37 by comoving, serves as a processing unit according to the present embodiment.

The image acquisition section 31 acquires image data generated by the infrared camera 13. For example, image data output from the infrared camera 13 at a specified frame rate is read as appropriate. The image data is data making up an image (the eyeball image 21) of the eyeball of the user 1. In other words, it can also be said that the image acquisition section 31 acquires the eyeball image 21. In the present embodiment, the eyeball image 21 is an example of eye information regarding an eye of the user. The image acquisition section 31 corresponds to an acquisition section. FIG. 5 schematically illustrates image data making up an image (the eyeball image 21) of the eye of the user 1.

The image processor 32 performs various types of image processes on the eyeball image 21 (image data). The image processor 32 includes a corneal region detector 40, a bright spot detector 41, and a pupil center detector 42.

The corneal region detector 40 detects the corneal region 8 of the eyeball 4 on the basis of the eyeball image 21. Specifically, a range is detected that corresponds to the corneal region 8 in the eye region 3 in the eyeball image 21. For example, it is possible to detect the corneal region 8 by extracting a boundary between the iris 6 and the sclera 9 (a white part of the eyeball), as illustrated in FIG. 4.

As described above, the eyeball image 21 is an infrared image captured by performing irradiation with the infrared light 15. For example, the use of a technology used in the field of iris authentication or the like makes it possible to easily detect the corneal region 8 from an infrared image (the eyeball image 21).

Figure 6:
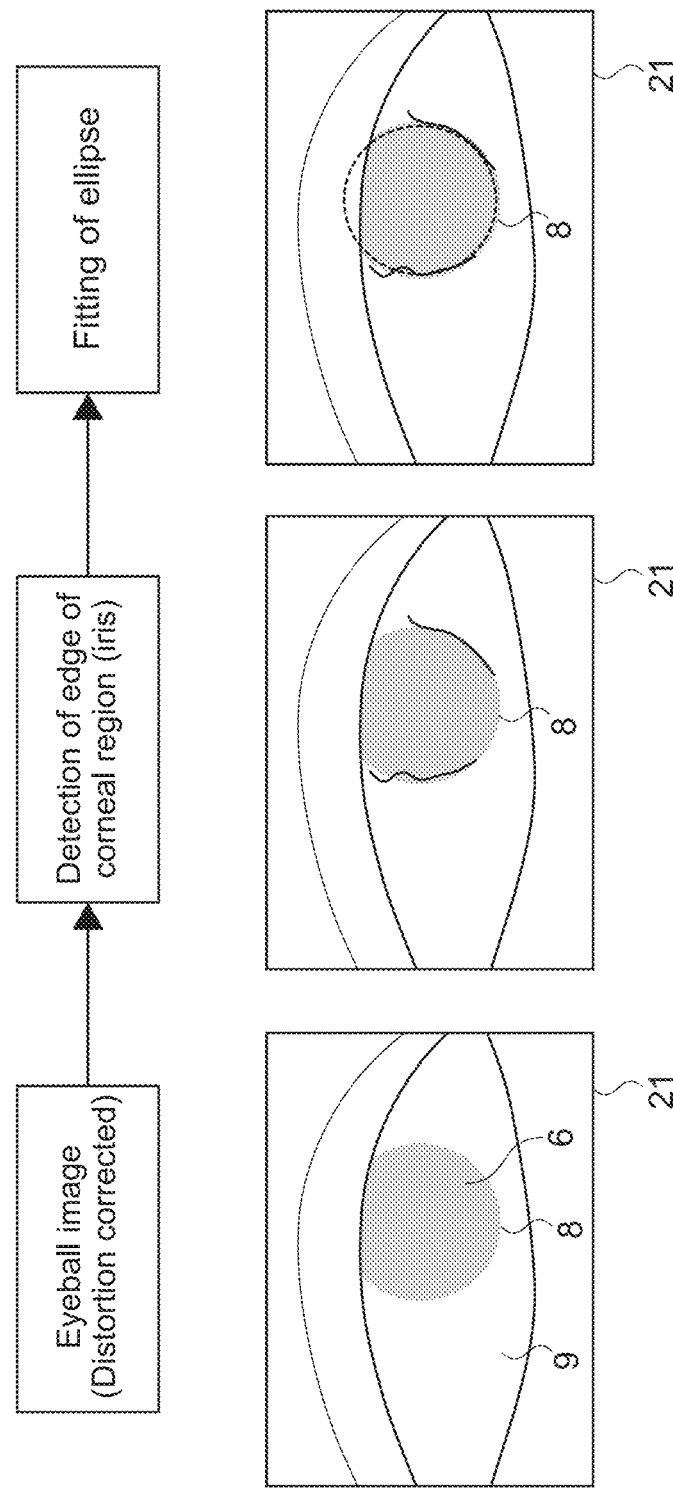
FIG. 6 schematically illustrates an example of processing of detecting a corneal region.

FIG. 6 schematically illustrates an example of processing of detecting the corneal region 8. On the left in FIG. 6, the eyeball image 21 in which distortion due to a lens or the like of the infrared camera 13 has been corrected is schematically illustrated. Note that an illustration of the pupil 5 and the like in the iris 6 is omitted in FIG. 6.

As illustrated in the center of FIG. 6, edge detection is performed on the eyeball image 21 in which distortion has been corrected, and a boundary between the iris 6 and a white part of the eyeball (the sclera 9) is extracted. Then, as illustrated on the right in FIG. 6, processing of fitting an ellipse to the extracted boundary of the iris 6 is performed. A region obtained by performing the fitting processing is calculated as the corneal region 8.

The specific method and the like for detecting the corneal region 8 are not limited. For example, a method of fitting a perfect circle to a boundary of the iris 6 or the like may be used. Further, for example, a method of extracting the iris 6 by performing image segmentation using a learner such as artificial intelligence (AI) that includes a machine learning function.

On the basis of the eyeball image 21, the bright spot detector 41 detects the bright spot 20 (a Purkinje image) generated due to the infrared light 15. Specifically, the position, the shape, and the like of the bright spot 20 in the eye region 3 in the eyeball image 21 are detected. For example, the position or the like of the bright spot 20 is detected on the basis of, for example, information regarding brightness in the eyeball image 21. As described above, in the present embodiment, a plurality of pieces of infrared light 15 is irradiated onto the eyeball 4 by a plurality of infrared light sources 12. The bright spot detector 41 detects, from the eyeball image 21, a plurality of bright spots 20 generated due to the plurality of pieces of infrared light 15.

Further, from among a plurality of bright spots 20 generated due to a plurality of pieces of infrared light 15, the bright spot detector 41 is capable of detecting, from the eyeball image 21, a pair of bright spots 20 provided in a specified arrangement. For example, from among a plurality of bright spots 20, the bright spot detector 41 detects a pair of bright spots 20 that are set according to the arrangement of the respective infrared light sources 12. For example, when two infrared light sources 12 are arranged for one eye 2, a pair of bright spots 20 is detected. Further, for example, when four infrared light sources 12 are arranged for one eye 2, two pairs of bright spots 20 are detected. The bright spots 20 that are paired up may be set as appropriate.

The method of detecting the bright spot 20 is not limited, and any detection processing using, for example, characteristics detection or machine learning may be used. Further, processing of detecting not only the position of the bright spot 20, but also the shape, the size, and the like of the bright spot 20 may be performed.

The pupil center detector 42 detects a pupil center 22 of the eyeball 4 on the basis of the eyeball image 21. Specifically, a pupil region corresponding to the pupil 5 is detected from the eyeball image 21, and the position of the center of the pupil 5 (the pupil center 22) is detected on the basis of the pupil region. FIG. 4 schematically illustrates, using a white cross, the pupil center 22 detected from the eyeball image 21. Note that the pupil center 22 does not necessarily coincide with the center of the corneal region 8 (the iris 6).

The method of detecting the pupil center 22 is not limited. For example, a method of detecting the pupil center 22 by fitting, for example, a perfect circle or an ellipse to the pupil 5, or a method of detecting the pupil center 22 using, for example, machine learning may be used as appropriate. Further, processing of detecting not only the pupil center 22, but also the shape, the size, and the like of the pupil 5 may be performed.

The first line-of-sight detector 33 determines a line-of-sight direction by a pupil-corneal reflection method on the basis of the eyeball image 21. The line-of-sight direction determined by the first line-of-sight detector 33 is hereinafter referred to as a first line-of-sight vector. In the present embodiment, the first line-of-sight vector corresponds to a first line-of-sight direction.

The pupil-corneal reflection method is, for example, a method of estimating a line-of-sight direction or the like by irradiating specified light (for example, the infrared light 15) onto the eyeball 4 of the user 1 and detecting the reflected light. More specifically, the pupil-corneal reflection method is a method that includes detecting a plurality of bright spots 20 generated due to a plurality of pieces of infrared light 15 from the eyeball image 21, and determining a first line-of-sight vector on the basis of the detected plurality of bright spots. In the present embodiment, the pupil-corneal reflection method corresponds to a first method.

Figure 7:
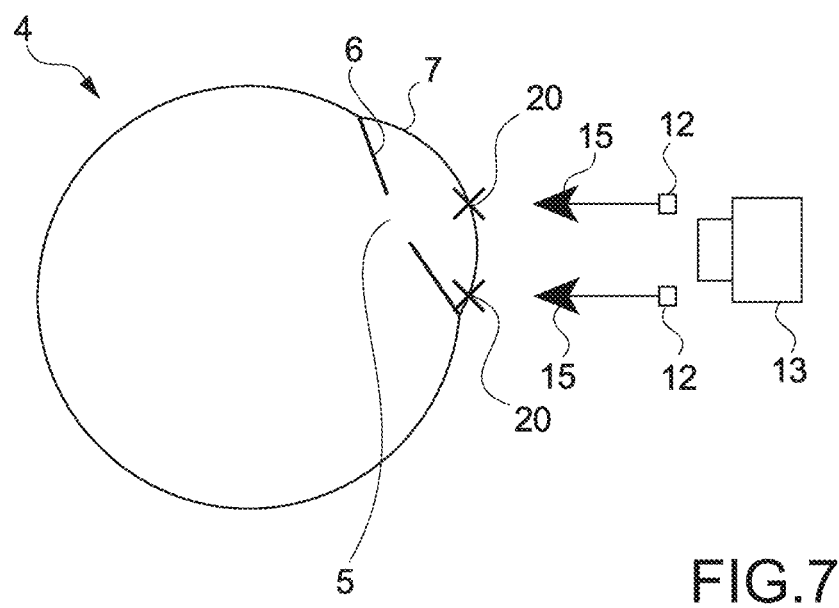
FIG. 7 schematically illustrates an eyeball of a user that is irradiated with infrared light.

FIG. 7 schematically illustrates the eyeball 4 of the user 1 that is irradiated with the infrared light 15. FIG. 7 schematically illustrates the eyeball 4 of the user 1 that is irradiated with the pieces of infrared light 15 from two infrared light sources 12. The eyeball 4 has a spherical shape, and the cornea 7 is formed on the surface of the eyeball 4. The cornea 7 is formed in a curved region in which a portion of the surface of the spherical eyeball 4 is expanded. The curved shape of the cornea 7 can be represented by, for example, a specified curvature. Note that, as illustrated in FIG. 7, the iris 6 and the pupil 5 (an opening portion in the center of the iris 6) are formed inside the cornea 7.

In the present embodiment, the first line-of-sight detector 33 detects a line-of-sight direction of the user 1 using a three-dimensional model of the eyeball 4 (an eyeball model) of the user 1. For example, a pose and the like of the eyeball model is estimated on the basis of a position (the bright spot 20) irradiated with the infrared light 15, and the first line-of-sight vector is determined on the basis of a result of the estimation.

As described above, the bright spot 20 generated on the surface of the eyeball 4 due to the infrared light 15 serves as a reference point used to calculate the first line-of-sight vector. In other words, it can also be said that the pupil-corneal reflection method is a method of determining a first line-of-sight vector on the basis of a reference point (the bright spot 20) set on the surface of the eyeball 4. It is possible to accurately estimate the orientation, a pose, and the like of the eyeball 4 on the basis of the bright spot 20 existing on the surface of the eyeball 4 (cornea). Further, even when, for example, there is a positional shift of the apparatus, it is possible to detect a line-of-sight direction with a high degree of accuracy using the bright spot 20.

Note that, for example, a result of detection performed by the bright spot detector 41 of the image processor 32 and a result of detection performed by the pupil center detector 42 of the image processor 32 (such as the position of the bright spot 20 and the position of the pupil center 22) are used to perform the processing of estimating a pose and the like of the eyeball model. The specific processing performed by the first line-of-sight detector 33 will be described later in detail.

Returning to FIG. 5, the second line-of-sight detector 34 determines a line-of-sight direction by detecting the position, the shape, and the like of the pupil 5 from the eyeball image 21. The line-of-sight direction determined by the second line-of-sight detector 34 is hereinafter referred to as a second line-of-sight vector. In the present embodiment, the second line-of-sight vector corresponds to a second line-of-sight direction.

Figure 8:
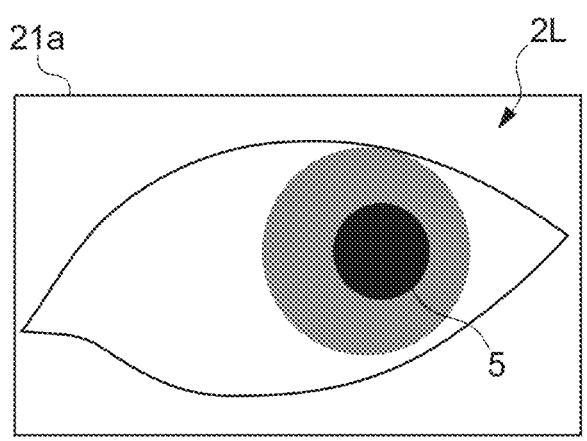
FIG. 8 schematically illustrates an example of an eyeball image.
Figure 8:
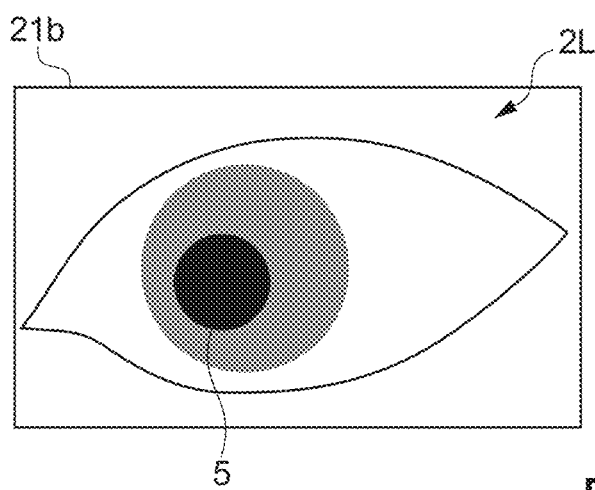

FIG. 8 schematically illustrates an example of the eyeball image 21. In eyeball images 21a and 21b respectively illustrated in A and B of FIG. 8, the lines of sight of the user 1 are oriented toward different directions. The eyeball images 21a and 21b are eyeball images 21 of the left eye 2L of the user 1.

For example, when the user 1 looks in a leftward direction as viewed from the user 1 (A of FIG. 8), the position of the pupil 5 is shifted to the right from the front in the eyeball image 21a of the left eye 2L. Conversely, when the user 1 looks in a rightward direction as viewed from the user 1 (B of FIG. 8), the position of the pupil 5 is shifted to the left from the front in the eyeball image 21b of the left eye 2L. As described above, when the line of sight of the user 1 is changed, the position of the pupil 5 in the eyeball image 21 is moved according to the line of sight.

For example, it is possible to estimate the line of sight of the user 1 by recording a direction in which the user 1 is looking (a line-of-sight direction) and a position of the pupil 5 in the eyeball image 21 in association with each other. In the present embodiment, a calibration table or the like used to convert the position of the pupil 5 of the user 1 into the line of sight of the user 1, is recorded in the storage 19 in advance. The second line-of-sight detector 34 determines a second line-of-sight vector from the position of the pupil 5 of the user 1 on the basis of the calibration table or the like. This processing is performed using, for example, a result of detection performed by the image processor 32 (such as a position of the pupil center 22).

The method of determining a line-of-sight direction (a second line-of-sight vector) by detecting a position or the like of the pupil 5 from the eyeball image 21 is hereinafter referred to as a pupil method. Thus, it can also be said that the second line-of-sight detector 34 detects a second line-of-sight vector on the basis of the eyeball image 21 using the pupil method. Note that, in the pupil method, the bright spot 20 or the like is not used as in the pupil-corneal reflection method used in the first line-of-sight detecting section 33. Thus, the pupil method is different from the pupil-corneal reflection method. In the present embodiment, the pupil method corresponds to a second method.

Returning to FIG. 5, the synthesis ratio calculator 35 calculates a synthesis ratio used to synthesize a first line-of-sight vector and a second line-of-sight vector. The synthesis ratio is a parameter that represents a ratio between a first line-of-sight vector and a second line-of-sight vector when the first line-of-sight vector and the second line-of-sight vector are synthesized. In other words, it can also be said that the synthesis ratio is a parameter that represents weight of each line-of-sight vector when the first and second line-of-sight vectors are synthesized.

In the present embodiment, a weighting coefficient used to synthesize a first line-of-sight vector and a second line-of-sight vector, is calculated as the synthesis ratio. The weighting coefficient is, for example, a coefficient used to assign weight to each line-of-sight vector when the first line-of-sight vector and the second line-of-sight vector are synthesized.

For example, it is assumed that $w_c$ represents a weighting coefficient of the first line-of-sight vector, and $w_i$ represents a weighting coefficient of the second line-of-sight vector. In this case, the synthesis ratio is represented by, for example, $w_c:w_i$. Note the first line-of-sight vector and the second line-of-sight vector are unit vectors that respectively represent line-of-sight directions calculated by, for example, respective methods. For example, coefficients that are normalized such that $w_c+w_i=1$ is satisfied are used as the respective weighting coefficients. Consequently, a line-of-sight direction obtained by perform synthesis (a synthesis line-of-sight vector) is also a unit vector, and thus it is possible to properly synthesize the respective line-of-sight vectors.

In the present embodiment, the synthesis ratio is calculated on the basis of a weighting coefficient $w_c$ of a first line-of-sight vector, where $w_c<1$. In this case, $w_i=1-w_c$ is set to be a weighting coefficient of a second line-of-sight vector. For example, when the degree of accuracy in detecting the first line-of-sight vector using the pupil-corneal reflex method is high, the weighting coefficient $w_c$ is set to a large value, and this results in an increase in the proportion of the first line-of-sight vector. Further, when the degree of accuracy in the detection is low, the weighting coefficient $w_c$ is set to a small value, and this results in a reduction in the proportion of the first line-of-sight vector. As described above, it can also be said that the weighting coefficient $w_c$ is a value that represents the reliability of the first line-of-sight vector. In the present embodiment, the weighting coefficient $w_c$ is an example of reliability information.

As illustrated in FIG. 5, the synthesis ratio calculator 35 calculates the weighting coefficient wc on the basis of a result of detection performed by the corneal region detector 40 of the image processor 32, a result of detection performed by the bright spot detector 41 of the image processor 32, and a result of detection performed by the pupil center detector 42 of the image processor 32. Thus, the weighting coefficient wc of a first line-of-sight vector is calculated on the basis of the eyeball image 21. In other words, the reliability of a first line-of-sight vector is calculated on the basis of the eyeball image 21. The method of calculating the weighting coefficient wc will be described later in detail with reference to, for example, FIGS. 12A and 12B.

On the basis of the weighting coefficient $w_c$, the line-of-sight synthesis section 36 synthesizes a first line-of-sight vector and a second line-of-sight vector, and determines a line-of-sight direction of the user 1. The line-of-sight direction obtained by synthesizing a first line-of-sight vector and a second line-of-sight vector is hereinafter referred to as a synthesis line-of-sight vector. The calculated synthesis line-of-sight direction is output as a result of detection of a line of sight that is performed by the controller 30.

The correction parameter update section 37 updates a correction parameter used to determine a second line-of-sight vector. Specifically, a parameter recorded in a calibration table used by the second line-of-sight detector 34 is updated. The calibration table is stored in, for example, the storage 19, and is generated by performing specified calibration processing.

Note that a calibration table used by the first line-of-sight detector 33 is also stored in the storage 19. Hereinafter, the calibration table for the first line-of-sight detector 33 is referred to as a first calibration table, and a parameter recorded in the first calibration table is referred to as a first correction parameter. Further, the calibration table for the second line-of-sight detector 34 is referred to as a second calibration table, and a parameter recorded in the second calibration table is referred to as a second correction parameter.

Figure 9A:
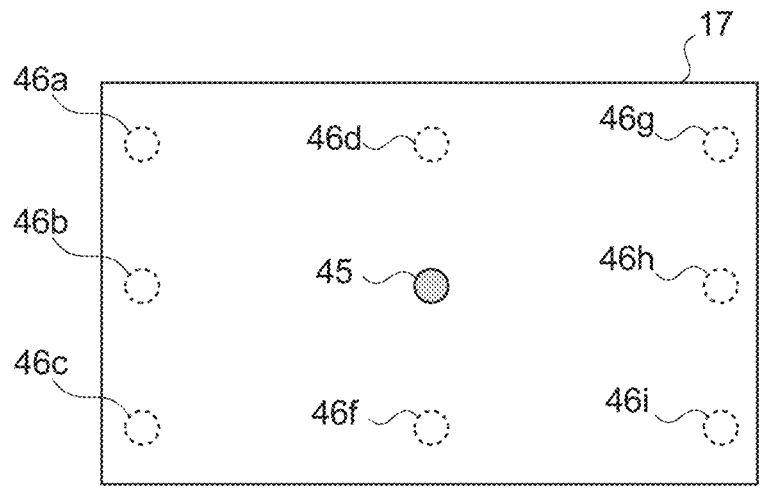
FIGS. 9A and 9B are schematic diagrams for describing an example of calibration processing.
Figure 9B:
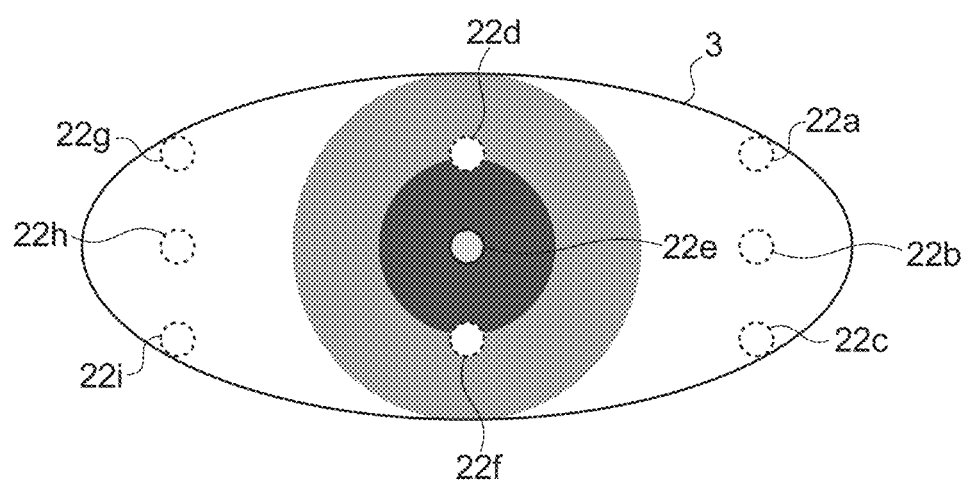

FIGS. 9A and 9B are schematic diagrams for describing an example of calibration processing. FIG. 9A schematically illustrates an example of a marker 45 displayed on the display 17 when the calibration processing is performed. FIG. 9B schematically illustrates an example of the eye region 3 of the user 1 when the calibration processing is performed. The calibration processing is performed as appropriate, for example, at a timing at which the user 1 starts using the HMD 100. Of course, the calibration processing may be performed at any timing according to, for example, an instruction given by the user 1.

In FIG. 9A, the markers 45 are displayed at nine display positions 46a to 46i on the display 17, the display positions 46a to 46i being set in an arrangement of 3×3. As viewed from the user 1, the display positions 46a to 46c are set from the top in a left column, the display positions 46d to 46f are set from the top in a center column, and the display positions 46g to 46i are set from the top in a right column.

The markers 45 are displayed at the respective display positions 46a to 46i in, for example, a specified order. In other words, a single marker 45 is displayed at a time. An instruction to gaze at a displayed marker 45 is presented to the user 1 while the calibration processing is being performed. Thus, the line of sight of the user 1 is moved according to the display position of the displayed marker 45 such that the user 1 gazes at the displayed marker 45.

In FIG. 9A, the marker 45 is displayed at the display position 46e in the center. In this case, as illustrated in FIG. 9B, the user 1 looks to the front to gaze at the marker 45e displayed at the front display position 46e (in the center of the display 17).

The second line-of-sight detector 34 detects a pupil center 22e when the user 1 is looking at the marker 45 displayed at the display position 46e, and determines a second line-of-sight vector. For example, a vector (a marker vector) that connects the pupil center 22e to the marker 45 (the display position 46e) is calculated as the second line-of-sight vector. When the marker 45 is displayed at the display position 46a situated in the upper left as viewed from the user 1, a pupil center 22a situated in the upper right of the eyeball image 21 is moved in the eyeball image 21.

In the calibration processing, for example, the markers 45 are sequentially displayed at the nine display positions 46a to 46i, and pupil centers 22a to 22i when the user 1 gazes at the markers 45 displayed at the respective display positions 46a to 46i, are respectively detected. Then, marker vectors from the respective pupil centers 22a to 22i to the respective display positions 46a to 22i are calculated as line-of-sight vectors for correction.

In the second calibration table, for example, nine line-of-sight vectors for correction that are determined according to the respective display positions 46a to 46i are stored in association with coordinates of the pupil centers 22a to 22i in the eyeball image 21. In other words, it can also be said that the second calibration table is a map in which a line-of-sight vector for each calibration position in the eyeball image 21 is recorded. The line-of-sight vector is used as a second correction parameter.

Thus, for example, when the pupil 5 is moved to the upper right pupil center 22a in the eye region 3 in the eyeball image 21, it is possible to calculate a line-of-sight vector oriented toward the upper left of the display 17 (the display position 46a). Note that, when the pupil 5 exists at a position between the pupil centers 22a to 22i, the second line-of-sight vector is calculated as appropriate using, for example, a method such as linear interpolation.

In the correction parameter update section 37, processing of updating, as appropriate, the second correction parameter acquired by performing the calibration processing, is performed. Thus, the second correction parameter is dynamically updated during an operation of the HMD 100.

Note that, in the calibration processing, the first calibration table or the like used in the first line-of-sight detector 33 is also generated. This point will be described later in detail with reference to, for example, FIG. 11.

Figure 10:
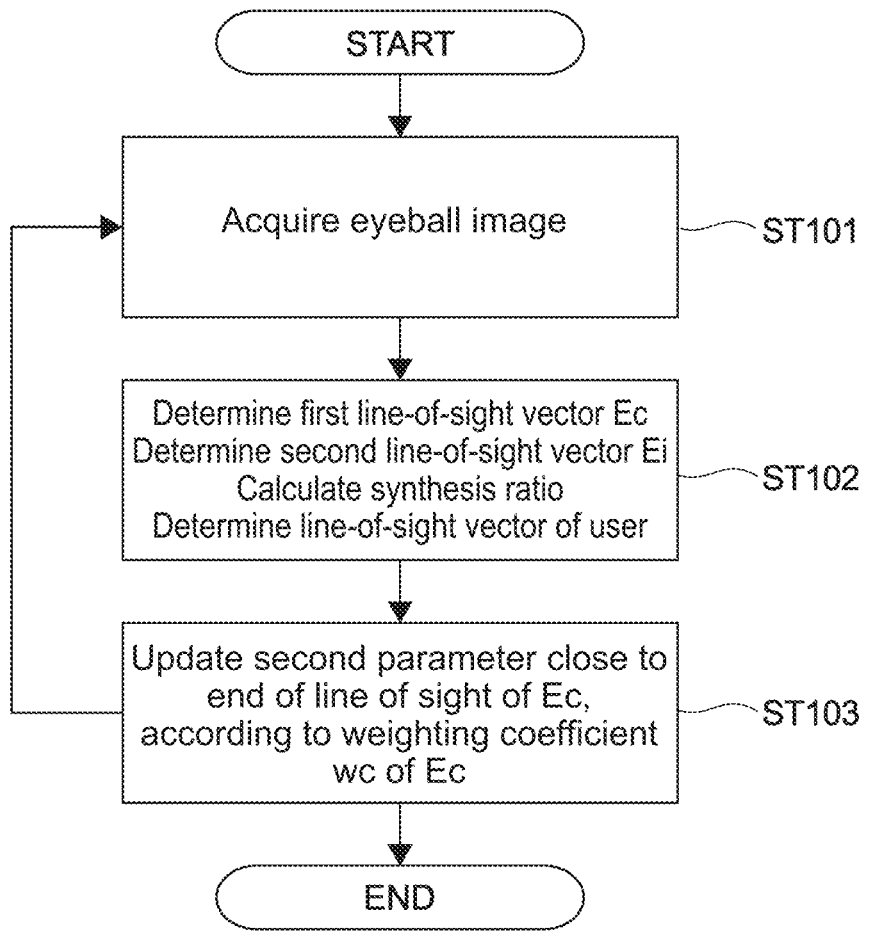
FIG. 10 is a flowchart illustrating an example of a basic operation of the HMD.

FIG. 10 is a flowchart illustrating an example of a basic operation of the HMD 100. Processing illustrated in FIG. 10 is, for example, loop processing that is continuously performed after the HMD 100 is started. In the following description, it is assumed that the calibration processing is completed.

First, the eyeball image 21 of the eyeball of the user 1 is acquired by the image acquisition section 31, the eyeball image 21 of the eyeball of the user 1 being captured in a state in which the eyeball of the user 1 is irradiated with a plurality of pieces of infrared light 15 (Step 101). For example, a plurality of pieces of infrared light 15 is irradiated onto the eye 2 of the user 1 with at a specified intensity by a plurality of infrared light sources 12, and an image of the eye 2 of the user 1 is captured by the infrared camera 13 in a state in which the eye 2 of the user 1 is irradiated with the infrared light 15. Image data of the captured image (the eyeball image 21) is output to the controller 30 by the infrared camera 13, and the eyeball image 21 is read by the image acquisition section 31.

A line-of-sight direction of the user 1 is determined on the basis of the acquired eyeball image 21 (Step 102). First, on the basis of the eyeball image 21, a first line-of-sight vector is determined by the first line-of-sight detector 33 using the pupil-corneal reflection method, and a second line-of-sight vector is determined by the second line-of-sight detector 34 using the pupil method. Processes of calculating the respective line-of-sight vectors may be performed in parallel or sequentially.

Figure 11:
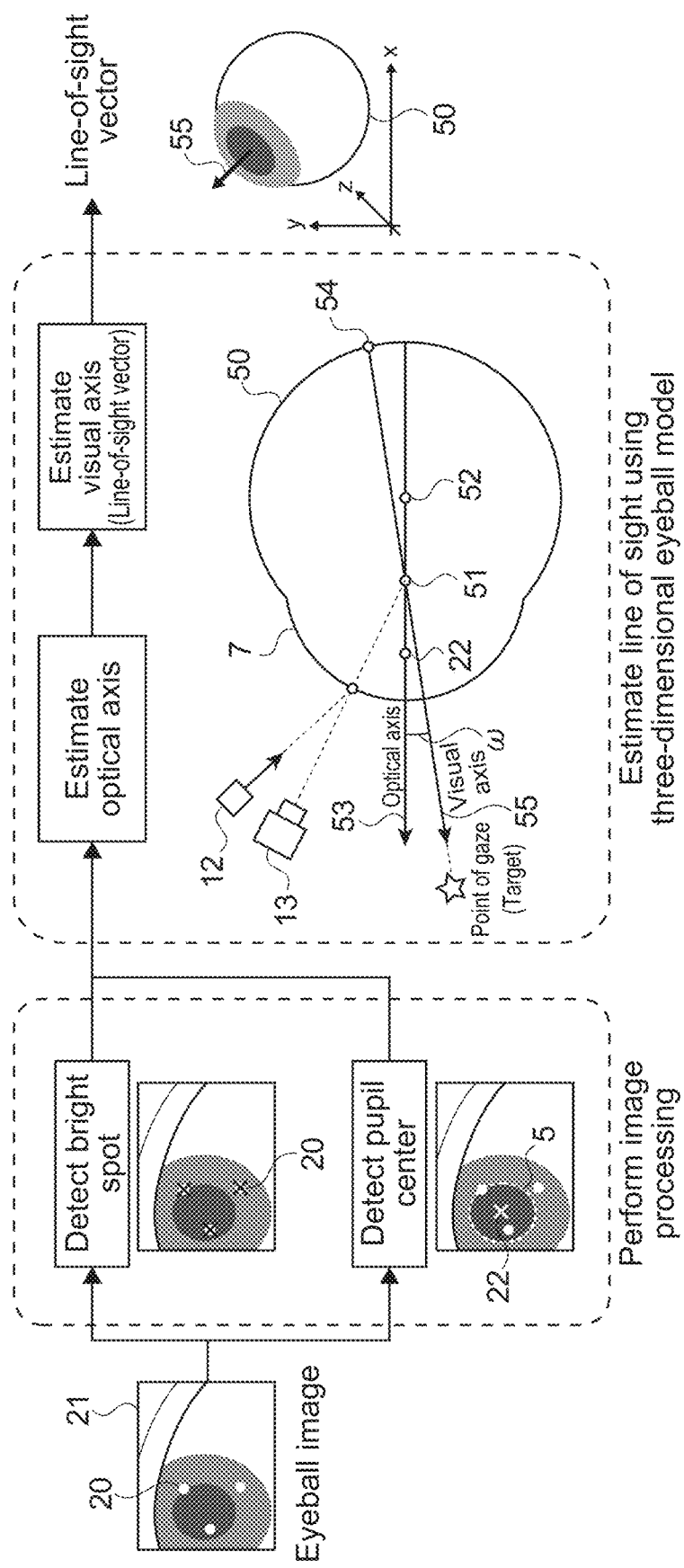
FIG. 11 schematically illustrates an example of processing of calculating a first line-of-sight vector using a pupil-corneal reflection method.

FIG. 11 schematically illustrates an example of the processing of calculating a first line-of-sight vector using the pupil-corneal reflection method. FIG. 11 schematically illustrates a processing flow until a first line-of-sight vector is calculated using the pupil-corneal reflection method.

The eyeball image 21 acquired by the image acquisition section 31 is input to the bright spot detector 41 and the pupil center detector 42 of the image processor 32. The position and the shape of the bright spot 20 in the eyeball image 21 are detected by the bright spot detector 41. The bright spot detector 41 performs a series of processes including, for example, various image processes performed on the eyeball image 21, a process of acquiring a brightness distribution in the eyeball image 21, and a process of detecting, on the basis of the brightness distribution, a pixel having a relatively large difference from surrounding pixels in brightness value.

Further, the position and the shape of the pupil 5 in the eyeball image 21 is detected by the pupil center detector 42. The pupil center detector 42 performs, for example, various image processes on the eyeball image 21 (such as a process of adjusting distortion, the black level, white balance, and the like), and a process of acquiring a brightness distribution in the eyeball image 21. Further, a process of detecting a contour (an edge) of an image of the pupil 5 on the basis of the acquired brightness distribution, a process of approximating the detected contour of the image of the pupil 5 with a figure such as a circle or an ellipse, or the like may be performed. The pupil center 22 is calculated from the detected image of the pupil 5.

When the bright spot 20 and the pupil 5 are detected, processing of estimating a line-of-sight direction (a first line-of-sight vector) of the user 1 is performed by the first line-of-sight detector 33. In the present embodiment, the first line-of-sight vector is estimated on the basis of a three-dimensional model of the eyeball 4 (an eyeball model 50). FIG. 11 schematically illustrates the eyeball model 50.

In the eyeball model 50, the cornea 7 is a portion of a sphere. The center of the sphere that represents the cornea 7 is hereinafter referred to as a corneal curvature center 51. Further, the pupil center 22 exists inside the sphere representing the cornea 7. As illustrated in FIG. 11, a direction determined by connecting the corneal curvature center 51 to the pupil center 22 is a direction of an optical axis 53 of the eyeball 4 that passes through the center of the eyeball 4 (the eye center 52). It is possible to estimate the optical axis 53 of the eyeball 4 using the pupil-corneal reflection method.

On the other hand, the line of sight of the user 1 is situated on a visual axis 55 that connects the corneal curvature center 51 to a fovea 54 situated in the eyeball 4. Thus, the optical axis 53 and the visual axis 55 (a line-of-sight direction of the user 1) of the eyeball 4 intersect at a specified angle. In other words, a vector oriented toward a point of gaze (a target) that the user 1 is gazing at does not necessarily coincide with a vector oriented toward a central axis (the optical axis 53) of the eyeball 4. There is a difference between individuals in a deviation of the visual axis 55 from the optical axis 53, and the visual axis 55 is generally inclined at an angle of about four to eight degrees. An amount of deviation of the visual axis 55 from the optical axis 53 is hereinafter referred to as $\omega$.

The amount of deviation $\omega$ is calibrated by performing the calibration processing described with reference to FIGS. 9A and 9B. In the calibration processing, for example, a line of sight of the user 1 who is looking at a certain marker 45 (a marker vector), and the optical axis 53 at that time are calculated. The amount of deviation $\omega$ is calculated on the basis of the marker vector and the optical axis 53. For example, parameters, such as a rotation angle and an elevation angle with respect to a specified plane, that are used to convert the optical axis 53 into a marker vector are used as the amount of deviation $\omega$.

Note that, since the eyeball 4 is rotated by pulling of the muscle, roll rotation is made depending on a viewing direction. Thus, values of the rotation angle and the elevation angle vary depending on a direction toward which the line of sight of the user 1 is oriented. Thus, in the calibration processing, markers are displayed at the display positions 46a to 46i to calculate the amount of deviation $\omega$ (the rotation angle and the elevation angle). The amount of deviation $\omega$ calculated at each position is recorded in the first calibration table as the first correction parameter.

As illustrated in FIG. 11, optical-axis estimation processing of estimating the optical axis 53 of the eyeball 4 and visual-axis estimation processing of estimating the visual axis 55 on the basis of the estimated optical axis 53 are performed in the first line-of-sight detector 33 as processing of estimating a first line-of-sight vector.

In the optical-axis estimation processing, a three-dimensional coordinate of the pupil center 22 in the eyeball model 50 is calculated on the basis of a result of detection performed by the pupil center detector 42. For example, three-dimensional coordinates of respective points on a contour of the pupil 5 that is extracted from the eyeball image 21 are calculated on the basis of, for example, an arrangement position of the infrared camera 13 (a positional relationship between the infrared camera 13 and the eyeball 4), the refraction of light on the surface of the cornea 7, and a distance between the corneal curvature center 51 and the pupil center 22. Then a coordinate of a point in the center from among the respective points on the contour of the pupil 5 is calculated as the three-dimensional coordinate of the pupil center 22. This makes it possible to calculate the three-dimensional coordinate of the pupil center 22 with a high degree of accuracy.

The method of calculating, for example, a three-dimensional coordinate of the pupil center 22 is not limited, and, for example, processing of converting, into a three-dimensional coordinate in the eyeball model 50, a position of the pupil center 22 in the eyeball image 21 that is calculated by performing image processing, may be performed. This makes it possible to shorten the time necessary to perform operation processing. Moreover, any method of calculating a three-dimensional coordinate of the pupil center 22 may be used.

Further, in the optical-axis estimation processing, a three-dimensional coordinate of the corneal curvature center 51 in the eyeball model 50 is calculated on the basis of a result of detection performed by the bright spot detector 41. For example, on the basis of, for example, a positional relationship among the infrared light source 12, the infrared camera 13, and the eyeball 4, and a radius of curvature of the cornea 7, a position on a line connecting the infrared camera 13 to the center of the bright spot 20 is calculated as a three-dimensional coordinate of the center of curvature of the cornea 51, the position being situated at a distance corresponding to the radius of curvature of the cornea 7 from the surface of the cornea 7 in a direction of the inside of the eyeball 4.

Note that, although the example in which there exists a single bright spot 20 has been described in FIG. 11, it is also possible to calculate a three-dimensional coordinate of the corneal curvature center 51 using a plurality of bright spots 20 (such as a pair of bright spots 20). For example, infrared light enters the eyeball 4 in a specified positional relationship depending on an arrangement of the infrared light source 12. The use of, for example, a pair of bright spots 20 in such a specified positional relationship makes it possible to calculate the corneal curvature center 51 and the like with a high degree of accuracy. Further, for example, even when one of paired bright spots 20 is not detected, it is possible to estimate a position of the undetected bright spot 20 and use it to perform the calculation processing. Moreover, any method of calculating a three-dimensional coordinate of the corneal curvature center 51 may be used.

As described above, three-dimensional coordinates of the pupil center 22 and the corneal curvature center 51 are calculated in the optical-axis estimation processing. Then, an optical-axis vector (the optical axis 53) that connects the corneal curvature center 51 to the pupil center 22 is estimated on the basis of the calculated three-dimensional coordinates.

In the visual-axis estimation processing, the visual axis 55 of the eyeball 4 is estimated from the estimated optical axis 53. For example, a line-of-sight vector of the user 1 (the visual axis 55) is estimated by rotating the optical axis 53 at a specified angle (such as a rotation angle and an elevation angle) on the basis of a first calibration parameter (the amount of deviation ω) recorded in the first calibration table. In other words, the visual-axis estimation processing can also be referred to as processing of converting, on the basis of the first calibration table, the optical axis 53 estimated using the pupil-corneal reflection method into the visual axis 55. The calculated line-of-sight vector is output as a first line-of-sight vector.

A line-of-sight vector of the user 1 (a second line-of-sight vector) is calculated by the second line-of-sight detector 34 on the basis of the pupil center 22 detected by the pupil center detector 42. For example, the second calibration table that is a map of a line-of-sight vector at each calibration position is referred to, and a line-of-sight vector corresponding to a position of the pupil center 22 in the eyeball image 21 is calculated as appropriate (refer to FIGS. 9A and 9B). The calculated line-of-sight vector is output as a second line-of-sight vector.

When the first line-of-sight vector and the second line-of-sight vector are calculated, processing of synthesizing the respective line-of-sight vectors is performed. First, a synthesis ratio between the first line-of-sight vector and the second line-of-sight vector (such as the weighting coefficient $w_c$) is calculated by the synthesis ratio calculator 35. The calculation of a synthesis ratio may be performed in parallel with the processing of calculating the first line-of-sight vector and the second line-of-sight vector.

Figure 12A:
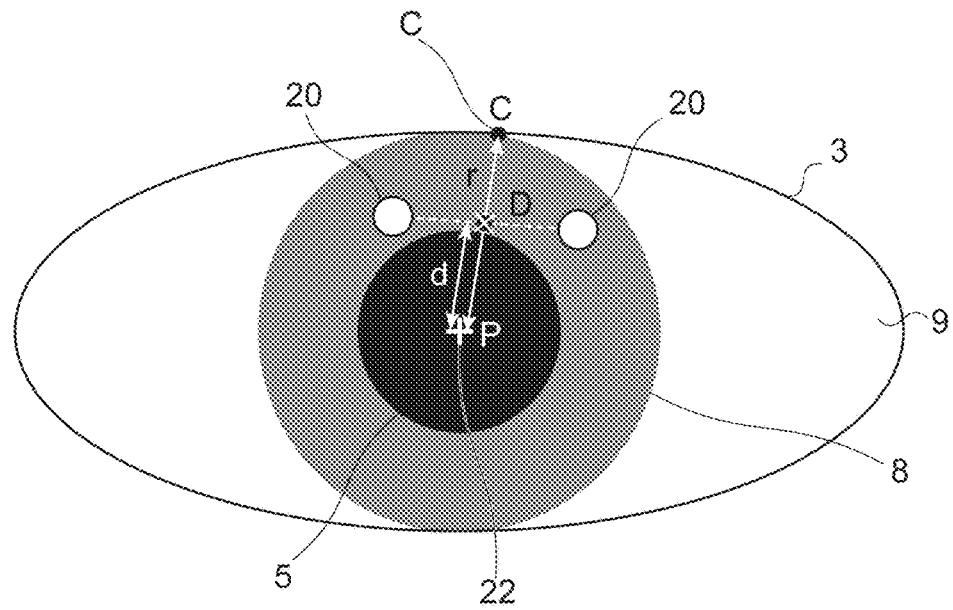
FIGS. 12A and 12B are schematic diagrams for describing an example of processing of calculating a synthesis ratio.
Figure 12B:
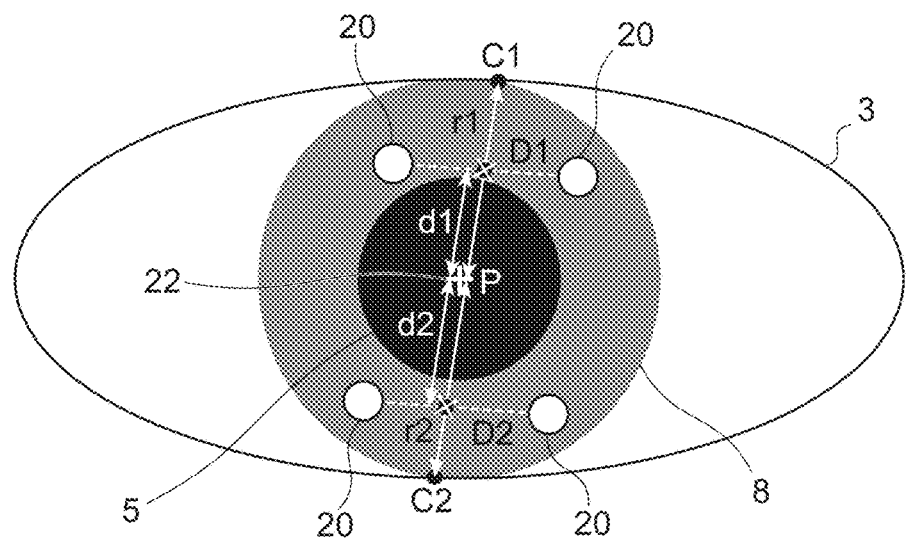

FIGS. 12A and 12B are schematic diagrams for describing an example of processing of calculating a synthesis ratio. FIG. 12A schematically illustrates the eyeball image 21 in which a pair of bright spots 20 has been detected. In the present embodiment, the weighting coefficient wc of a first line-of-sight vector is calculated on the basis of the positions of the paired bright spots 20 in the corneal region 8.

In the example illustrated in FIG. 12A, the weighting coefficient wc is calculated using a pupil center point P that represents the pupil center 22, a midpoint D between the paired bright spots 20, and an intersection C of a line passing through P and D and the corneal circumference (the corneal region 8). Note that the midpoint D between the paired bright spots 20 corresponds to a position of the pair of bright spots 20.

It is assumed that d represents a distance between the pupil center point P and the midpoint D of the paired bright spots 20 (a distance between P and D), and r represents a distance between the pupil center point P and the intersection C on the corneal circumference (a distance between P and C). The weighting coefficient $w_c$ of a first line-of-sight vector calculated using the pupil-corneal reflection method is represented by the following formula using r and d.

[Formula 1]

$$w_c = \frac{r-d}{r} \qquad (1)$$

As illustrated in FIG. 12A, the distance r between P and C exhibits substantially the same value as the radius of the corneal region 8. Thus, the distance r does not exhibit a value that varies greatly for each process. Note that, since there is a possibility that an elliptical region will be detected as the corneal region 8, the distance r is not necessarily a constant value.

On the other hand, the distance d between P and D is a parameter that varies for each process since the position of the pupil center point P is changed when the line of sight of the user 1 is changed. Thus, in Formula (1), the weighting coefficient $w_c$ is larger if the distance d is smaller, that is, if the position of a pair of bright spots 20 (the midpoint D) is closer to the pupil center point P. In other words, it can also be said that weight of a first line-of-sight coefficient is increased when the pair of bright spots 20 is generated near the pupil center 22.

Conversely, the weighting coefficient $w_c$ is smaller if the position of the pair of bright spots 20 (the midpoint D) is further away from the pupil center point P. In other words, when the pair of bright spots 20 is generated away from the pupil center 22, the weight of the first line-of-sight coefficient is set low. Note that when the distance d is not within the corneal region 8 and d>r is satisfied, or when one of the bright spots 20 is not detected, processing of setting the weighting coefficient $w_c$ to zero is performed.

As described above, the weighting coefficient $w_c$ is calculated by the synthesis ratio calculator 35 on the basis of the distance of a pair of bright spots 20 with respect to the pupil center 22. In other words, the weighting coefficient $w_c$ of a first line-of-sight vector is determined according to the distance from the pupil center 22 to the midpoint D of a pair of bright spots 20.

For example, the corneal region 8 having a spherical shape exists in the eyeball model 50 described with reference to FIG. 11. In the actual eyeball 4, the cornea 7 is smoothly connected to a region of the sclera 9 (a white part of the eyeball) around the corneal region 8. Thus, it is conceivable that the actual eyeball 4 has a shape different from the shape of the model in a spherical shape. Thus, when the position of the bright spot 20 is close to the periphery of the corneal region 8, a degree of the accuracy in detecting a first line-of-sight vector may be lower than that of a region close to the pupil center 22.

As indicated in Formula (1), the weighting coefficient $w_c$ of a first line-of-sight vector is set to be smaller as the distance from the pupil center 22 becomes larger. Thus, the weighting coefficient $w_c$ of a first line-of-sight vector serves as a parameter representing the reliability such as the accuracy in detecting a first line-of-sight vector. In other words, it can also be said that information regarding the reliability of a first line-of-sight vector (the weighting coefficient $w_c$) is calculated by the synthesis ratio calculator 35.

The method of calculating the weighting coefficient $w_c$ is not limited to the method performed using Formula (1). For example, the weighting coefficient $w_c$ may be set on the basis of, for example, the area of a triangle formed by connecting the pupil center point P and the respective bright spots 20, with the pupil center point P and the respective bright spots 20 being used as vertexes. In this case, the weighting coefficient is set as appropriate such that weight of a first line-of-sight vector is increased when the area of the triangle is small, and the weight of the first line-of-sight vector is reduced when the area of the triangle is large. This makes it possible to set a weighting coefficient including not only the distance between a pair of bright spots 20 and the pupil center (the height of the triangle), but also the distance between the bright spots 20 (the base of the triangle). This results in being able to synthesize first and second line-of-sight vectors with a high degree of accuracy.

When the weighting coefficient $w_c$ of a first line-of-sight vector is calculated, the weighting coefficient $(1-w_c)$ of a second line-of-sight vector is calculated. The ratio $(w_c:1-w_c)$ between the weighting coefficients of the respective line-of-sight vectors is a mixture ratio.

The first line-of-sight vector and the second line-of-sight vector are synthesized by the line-of-sight synthesis section 36. Hereinafter, a three-dimensional vector representing the first line-of-sight vector is referred to as a first line-of-sight vector $E_c$, and a three-dimensional vector representing the second line-of-sight vector is referred to as a second line-of-sight vector $E_i$. Further, a three-dimensional vector representing a line-of-sight direction obtained by performing synthesis is referred to as a synthesis line-of-sight vector E. The synthesis line-of-sight vector E is calculated as indicated below.

[Formula 2]

$$E = w_c E_c + (1-w_c) E_i \qquad (2)$$

As described above, the weighting coefficient $w_c$ is a function that varies slowly. Thus, a vector (synthesis line-of-sight vector E) is calculated that is obtained by seamlessly synthesizing the first line-of-sight vector $E_c$ and the second line-of-sight vector $E_i$ according to a value of the weighting coefficient $w_c$. As described above, in the present embodiment, the line-of-sight direction of the user 1 is determined on the basis of the weighting coefficient $w_c$. The calculated synthesis line-of-sight vector E is output as a result of detection performed in the controller 30, and is used for other applications and the like.

FIG. 12B schematically illustrates the eyeball image 21 in which two pairs of bright spots 20 are detected. Hereinafter, a pair of left and right bright spots 20 generated in an upper portion of the figure is referred to as a first pair, and a pair of left and right bright spots 20 generated in a lower portion of the figure is referred to as a second pair.

For example, as illustrated in FIG. 12B, a distance d1 between the pupil center point P and a midpoint D1 of the first pair is calculated, and a distance r1 from the pupil center point P to an intersection C1 of a line passing through P and D1 and the corneal circumference is calculated. Then, a weighting coefficient wc1 of the first pair is set using Formula (1). Further, a distance d2 between the pupil center point P and a midpoint D2 of the second pair is calculated, and a distance r2 from the pupil center point P to an intersection C2 of a line passing through P and D2 and the corneal circumference is calculated. Then, a weighting coefficient wc2 of the second pair is set.

As described above, when there exist two pairs of bright spots 20, it is possible to calculate a weighting coefficient for each pair. For example, the synthesis line-of-sight vector is calculated using the following formula, by use of the weighting coefficient $w_{c1}$ of the first pair and the weighting coefficient $w_{c2}$ of the second pair.

[Formula 3]

$$E = \max(w_{c1}, w_{c2}) \frac{w_{c1} E_{c1} + w_{c2} E_{c2}}{w_{c1} + w_{c2}} + (1 - \max(w_{c1}, w_{c2})) E_i \qquad (3)$$

Here, $E_{c1}$ is a line-of-sight vector calculated using the first pair, and $E_{c2}$ is a line-of-sight vector calculated using the second pair. In addition, $\max(w_{c1}, w_{c2})$ is a function that selects a weighting coefficient having a larger value from the weighting coefficients.

Using Formula (3), the two line-of-sight vectors $E_{c1}$ and $E_{c2}$ that are calculated by the first line-of-sight detector 33 using the pupil-corneal reflection method are synthesized by the first line-of-sight detector 33 according to the respective weighting coefficients. Using a result of the synthesis as the first line-of-sight vector, processing of synthesizing the first line-of-sight vector and the second line-of-sight vector $E_i$ calculated by the second line-of-sight detector 34 using the pupil method is further performed. This makes it possible to stably calculate a line-of-sight direction of the user 1 with a high degree of accuracy. For example, it is possible to synthesize each line-of-sight vector using such a method.

The present technology is also applicable to the case in which there exist three or more pairs of bright spots 20. In other words, it is possible to generalize a formula used to synthesize the line-of-sight vector calculated using the pupil-corneal reflection method and the second line-of-sight vector calculated using the pupil method as indicated below.

[Formula 4]

$$E = \max(w_{c1}, \ldots, w_{cn}) \frac{\sum_1^n w_{ck} E_{ck}}{\sum_1^n w_{ck}} + (1 - \max(w_{c1}, \ldots, w_{cn})) E_i \qquad (4)$$

This makes it possible to detect a line of sight with a high degree of accuracy using three or more pairs of bright spots 20. Further, even in such a case, it is possible to seamlessly synthesize the line-of-sight vector calculated using the pupil-corneal reflection method and a result of detection of a line of sight (the second line-of-sight vector $E_i$) that is performed using the pupil method.

Furthermore, it is also possible to calculate a weighting coefficient not only on the basis of the position of the bright spot 20 (a position of a pair of bright spots 20) as indicated in Formula (1), but also on the basis of the size of the bright spot 20. The size of the bright spot 20, that is, the area of the bright spot 20 (such as the number of pixels) is calculated as appropriate on the basis of, for example, the shape of the bright spot 20 detected by the bright spot detector 41. Hereinafter, s represents the area of the bright spot 20 used to calculate a first line-of-sight vector, $s_e$ represents an expected value of the area of the bright spot 20, and $s_{min}$ and $s_{max}$ respectively represent an effective minimum area and an effective maximum area of the bright spot 20.

The expected value $s_e$ of the area of the bright spot 20 is, for example, the area of the bright spot 20 when the eyeball 4 of the user 1 who is wearing the HMD 100 is properly irradiated with the infrared light 15. Further, the effective minimum area $s_{min}$ and the effective maximum area $s_{max}$ of the bright spot 20 are, for example, the minimum area and maximum area of the bright spot 20 that can be used to perform the processing of calculating a line-of-sight direction. The expected value $s_e$ of the area, the effective minimum set appropriately according to, for example, the characteristics of the HMD 100.

It is possible to calculate an area weight $w_s$ with respect to a single bright spot 20 using these parameters as indicated below.

[Formula 5]

$$w_s = \begin{cases} \frac{s - s_{min}}{s_e - s_{min}} & \text{if } s_{min} \leq s \leq s_e \\ \frac{s_{max} - s}{s_{max} - s_e} & \text{if } s_e < s \leq s_{max} \\ 0 & \text{else} \end{cases} \quad (5)$$

As indicated in Formula (5), when the area s of the bright spot 20 is in a range between the minimum effective area $s_{min}$ and the maximum effective area $s_{max}$, a heavier area weight $w_s$ is set for the bright spot 20 as the area of the bright spot 20 exhibits a value closer to the expected value $s_e$. Further, when the area s of the bright spot 20 is outside of the range the minimum effective area $s_{min}$ and the maximum effective area $s_{max}$, the area weight $w_s$ is set to zero.

An average of the area weight $w_s$ with respect to the pair of bright spots 20 is calculated from area weights $w_s$ of individual bright spots 20 set on the basis of the Formula (5), and is used as an area weight $w_{s\_pair}$ with respect to the pair. For example, the area weight $w_{s\_pair}$ of a pair is calculated as indicated below.

[Formula 6]

$$w_{s\_pair} = \sqrt{w_{s1} w_{s2}} \quad (6)$$

Here, $w_{s1}$ and $w_{s2}$ are area weights $w_s$ of the respective bright points of a pair. A geometrical mean of area weights $w_s$ of respective pairs is calculated using Formula (6). The calculation method is not limitative, and the area weight $w_{s\_pair}$ of a pair may be calculated by another method.

An weighting coefficient (an integration weighting coefficient $w_c'$) of a line-of-sight vector that is calculated using a pair of certain bright spots 20 is calculated as an average (such as a geometrical mean) of an area weight $w_{s\_pair}$ of a pair that is calculated using Formula (6), and a weighting coefficient $w_c$ of the pair (distance weight of the pair) that is calculated using Formula (1). In other words, the integration weighting coefficient $w_c'$ is calculated as indicated below.

[Formula 7]

$$w_c' = \sqrt{w_c w_{s\_pair}} \quad (7)$$

The integration weighting coefficient $w_c'$ is a parameter that represents the reliability obtained by integrating, for example, the reliability corresponding to the position of a pair of bright spots 20 and the reliability of the respective bright spots 20 making up the pair. As described above, in the present embodiment, the area of the bright spot 20 is calculated, and the weighting coefficient $w_c'$ is calculated on the basis of the calculated area of the bright spot 20. This makes it possible to calculate, with a high degree of accuracy, the reliability of a first line-of-sight vector calculated using the pupil-corneal reflection method, and to properly synthesize line-of-sight vectors.

The synthesis line-of-sight vector E is calculated using the integration weighting coefficient $w_c'$ as indicated below.

[Formula 8]

$$E = \max(w_{c1}', \ldots, w_{cn}') \frac{\sum_1^n w_{ck}' E_{ck}}{\sum_1^n w_{ck}'} + (1 - \max(w_{c1}', \ldots, w_{cn}'))E_i \quad (8)$$

As described above, in the present embodiment, a first line-of-sight vector and a second line-of-sight vector are synthesized on the basis of the reliability of the first line-of-sight vector (such as the weighting coefficient $w_c$). This makes it possible to improve the reliability of synthesized line-of-sight vectors.

Note that synthesis of the respective line-of-sight vectors is not limited to being performed on the basis of the reliability of the first line-of-sight vector, and the respective line-of-sight vectors may be synthesized using the reliability of the second line-of-sight vector. For example, it is possible to use, as the reliability of the second line-of-sight vector, the accuracy in fitting upon detecting the pupil 5, the accuracy in calculating the pupil center 22, or the like. For example, when the reliability of the second line-of-sight vector is high, weighting coefficients of the respective line-of-sight vectors are set as appropriate such that the proportion of the second line-of-sight vector is increased and the proportion of the first line-of-sight vector is reduced, and the respective line-of-sight vector are synthesized. For example, such processing may be performed.

Returning to FIG. 10, when the line-of-sight vector (the synthesis line-of-sight vector E) of the user 1 is calculated, processing of updating a second correction parameter is performed (Step 103). In the present embodiment, the second correction parameter is updated on the basis of a first line-of-sight vector.

As described using, for example, FIGS. 9A and 9B, the second correction parameter is a parameter recorded in the second calibration table used to perform processing of calculating a second line-of-sight vector using the pupil method. Specifically, the line-of-sight vector at each calibration position on an image (the eyeball image 21) is stored as the second correction parameter.

Figure 13A:
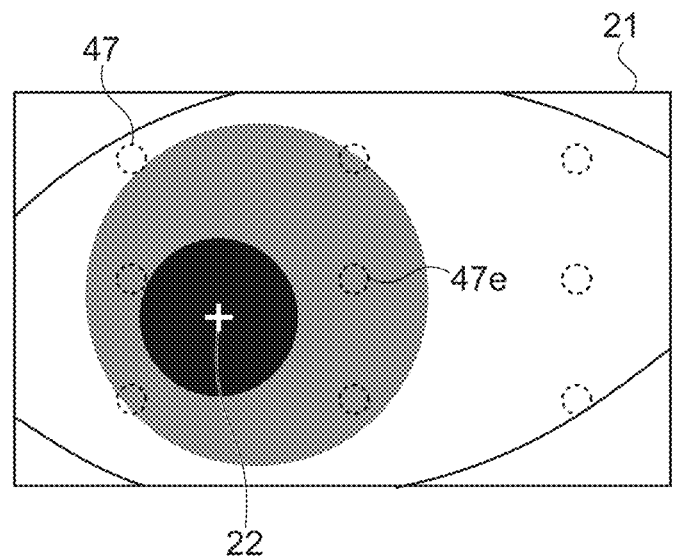
FIGS. 13A and 13B are schematic diagrams for describing processing of updating a second correction parameter.
Figure 13B:
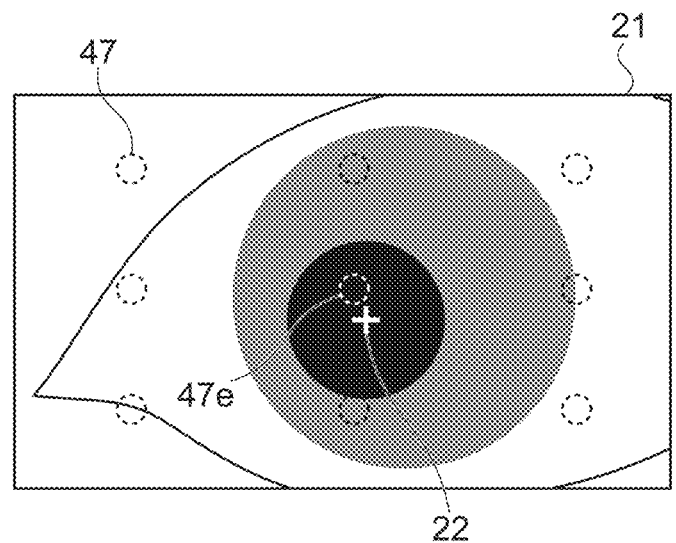

FIGS. 13A and 13B are schematic diagrams for describing processing of updating a second correction parameter. FIG. 13A schematically illustrates the eyeball image 21 captured when calibration processing is performed. FIG. 13B schematically illustrates the eyeball image 21 captured after the calibration processing is performed. It is assumed that, in FIGS. 13A and 13B, the user 1 is looking in the same direction.

FIG. 13A schematically illustrates the position of the pupil center 22 of the user 1 (hereinafter referred to as a calibration point 47) when markers are displayed at nine positions. For example, immediately after the calibration processing is performed, second correction parameters stored correspondingly to the respective calibration points 47 (line-of-sight vectors) are each oriented toward a proper direction.

Thus, it is possible to properly calculate the direction toward which the pupil center 22 illustrated in FIG. 13A is oriented, that is, the second line-of-sight vector on the basis of the second correction parameter at the calibration point 47 around the pupil center 22.

On the other hand, when a mounting position or the like of the HMD 100 is shifted, a relative position of the eyeball 4 with respect to the infrared camera 13 is changed. Consequently, an image-capturing range of the infrared camera 13 is shifted, and a range of the eye region 3 in the eyeball image 21 is changed as illustrated in FIG. 13B.

For example, when the line-of-sight direction of the pupil center 22 illustrated in FIG. 13B is calculated from a non-updated second correction parameter at the time of calibration, a result of the calculation indicates a direction different from an actual line-of-sight direction.

When, for example, the mounting position of the HMD 100 is shifted, as described above, there may be a reduction in the accuracy of a line-of-sight vector (the second correction parameter) recorded in the second calibration table. Thus, in the present embodiment, the second correction parameter is updated using a first line-of-sight vector calculated using the pupil-corneal reflection method different from the pupil method.

In the method using the pupil-corneal reflection method, a first line-of-sight vector is calculated on the basis of the bright spot 20 generated in the eyeball 4 of the user 1, that is, on the basis of a reference point set on the surface of the eyeball 4. Thus, even when, for example, a mounting position or the like of the HMD 100 is shifted, the first line-of-sight detector 33 is capable of estimating a first line-of-sight vector with a sufficiently high degree of accuracy, compared to the case of a second line-of-sight vector calculated on the basis of a position in the eyeball image 21. In other words, it can be said that the pupil-corneal reflection method is a highly accurate line-of-sight detection method that makes it possible to successfully deal with a shift of an eyeball.

In the present embodiment, a second correction parameter is updated by the correction parameter update section 37 according to the reliability of a first line-of-sight vector. Specifically, a second correction parameter is updated on the basis of a weighting coefficient used to synthesize a first line-of-sight vector and a second line-of-sight vector. For example, the weighting coefficient $w_c$ that is represented by Formula (1) and calculated on the basis of a position of the bright spot 20, the area weight $w_{s\_pair}$ with respect to a pair of the bright spot 20, or the integration weighting coefficient $w_c'$ obtained by integrating $w_c$ and $w_{s\_pair}$ is used as appropriate as a weighting coefficient. In the following description, the weighting coefficient $w_c$ is used as an example.

For example, it is assumed that a first line-of-sight vector is calculated in the state illustrated in FIG. 13B. In this case, the second correction parameter at the calibration point 47 close to an end of a line of sight of the first line-of-sight vector is updated. In the example illustrated in FIG. 13B, of the nine calibration points 47, a line-of-sight vector for correction stored in association with the calibration point 47e situated in the center from among the nine calibration points 47 is updated in according to the first line-of-sight vector Ec that is the first line-of-sight vector.

For example, the line-of-sight vector for correction is rotated about a specified axis as appropriate according to the first line-of-sight vector $E_c$. The rotation amount (such as a rotation angle and an elevation angle) is set according to the weighting coefficient $w_c$ of the first line-of-sight vector. For example, when the weighting coefficient $w_c$ is high and the reliability (the accuracy in calculation) of the first line-of-sight vector $E_c$ is high, the line-of-sight vector for correction is rotated to be oriented toward a direction extending substantially in parallel with the first line-of-sight vector $E_c$. Further, for example, when the weighting coefficient $w_c$ is low and the reliability of the first line-of-sight vector $E_c$ is low, the rotation amount of the line-of-sight vector for correction is set to a small value, or the line-of-sight vector for correction is not rotated.

The method of updating a second correction parameter (a line-of-sight vector for correction) is not limited. For example, when the weighting coefficient $w_c$ is greater than a specified threshold (for example, $w_c > 0.5$), threshold processing such as updating a line-of-sight vector for correction may be performed. Further, for example, the rotation amount of a line-of-sight vector for correcting may be calculated using, for example, linear interpolation according to, for example, the position of the pupil center 22 for which the first line-of-sight vector $E_c$ is calculated. Moreover, any method of updating a second correction parameter may be used.

Further, on the basis of the rotation amount of a line-of-sight vector for correction used to update the calibration point 47 close to the first line-of-sight vector, the second correction parameter at the other calibration point 47 is updated as appropriate. In other words, the orientation of each vector recorded in the second calibration table is rotated according to the first line-of-sight vector. This makes it possible to easily update the entire second calibration table.

Note that the reliability of the first line-of-sight vector is not limited to the case of using the weighting coefficient $w_c$. For example, the second correction parameter may be updated according to the position of the pupil 5 in the eye region 3 in the eyeball image 21, the eye region 3 including the eyeball 4. As described above, in the processing of calculating a first line-of-sight vector (the pupil-corneal reflection method), the weighting coefficient $w_c$ is set to be larger if the bright spot 20 is situated closer to the pupil center 22.

Thus, it is possible to represent the accuracy and the like of the position of the first line-of-sight vector using the position of the pupil center 22. In this case, the position of the pupil center 22 serves as a parameter that represents the reliability of the first line-of-sight vector. For example, when the pupil 5 is in a range in which the bright spot 20 is included in the corneal region 8, the second correction parameter is updated according to the position of the pupil 5. This makes it possible to easily update the second correction parameter.

Moreover, any parameter or the like that represents the reliability of the first line-of-sight vector may be used. As described above, it is possible to update the second correction parameter to an appropriate value by performing the update processing using the reliability of the first line-of-sight vector. This results in being able to improve the accuracy of the second line-of-sight vector.

As illustrated in FIG. 10, when the second correction parameter is updated, the process returns to Step 101, and a next eyeball image 21 is acquired. As described above, in the present embodiment, the second correction parameter is updated for each execution of loop processing. This makes it possible to perform automatic calibration in which the second correction parameter is automatically updated. This results in being able to perform a stable line-of-sight detection that makes it possible to successfully deal with a positional shift and the like of the eyeball 4.
that is strong in a shift of the position of an eyeball As described above, in the controller 30 according to the present embodiment, the eyeball image 21 of the user 1 is acquired, and a first line-of-sight vector and a second line-of-sight vector are determined on the basis of the eyeball image 21 of the user 1, respectively using the pupil-corneal reflection method and the pupil method that are different from each other. Further, a weighting coefficient regarding at least one of the reliability of the first line-of-sight vector or the reliability of the second line-of-sight vector is calculated, and a line-of-sight direction of the user is determined on the basis of the weighting coefficient. This makes it possible to stably detect a line of sight.

Figure 14:
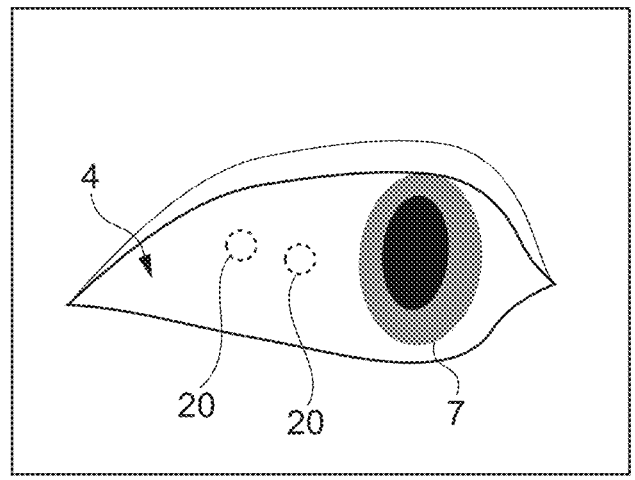
FIG. 14 schematically illustrates a comparative example of an eyeball image of the user.

In the method of detecting a line-of-sight direction of the user 1 by detecting reflected light of light irradiated onto an eyeball, it may be difficult to properly detect the reflected light, depending on the position of a line of sight of the user 1. FIG. 14 schematically illustrates a comparative example of an eyeball image of the user 1. As illustrated in FIG. 14, the bright dot 20 may be outside of a range of the cornea 7 when the user looks away from the front. Thus, there may a reduction in the accuracy in detecting the bright spot 20 and thus in the accuracy in detecting a line-of-sight direction.

Further, the distance between the camera and the eyeball differs for each user 1 since the position of the eye in depth and the height of the nose differ for each user 1, and there is a difference between individuals in a position onto which the bright spot 20 is irradiated. Thus, even when the user is looking to the front, it may be difficult to accurately irradiate the cornea 7 with the infrared light 15.

Figure 15A:
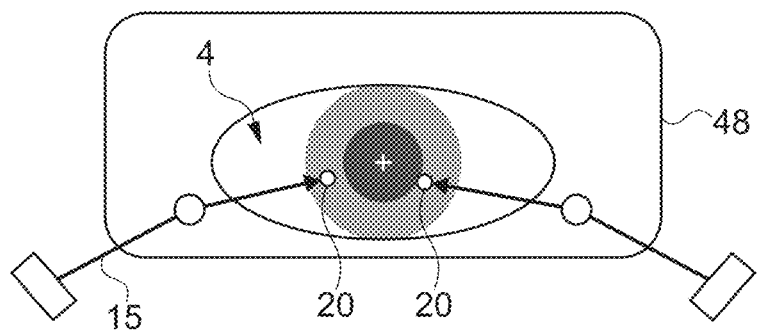
FIGS. 15A and 15B schematically illustrate a comparative example of irradiation performed with infrared light.
Figure 15B:
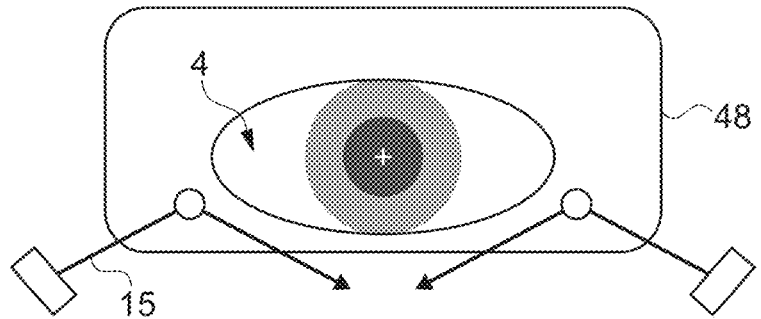

FIGS. 15A and 15B schematically illustrate a comparative example of irradiation performed with the infrared light 15. FIGS. 15A and 15B each schematically illustrate a state in which the eyeball 4 of the user 1 using glasses 48 is irradiated with the infrared light 15. For example, as illustrated in FIG. 15A, the position onto which the infrared light 15 is irradiated may be shifted due to light refraction caused by the glasses 48 (lens). Further, for example, as illustrated in FIG. 15B, when, for example, the infrared light 15 enters the glasses 48 at a small angle, there is a possibility that the infrared light 15 will not reach the cornea 7 due to total reflection on the surface of the glasses 48.

For example, in a method of detecting a line-of-sight direction by extracting a feature (such as a pupil) from an image of the eyeball 4, the line-of-sight direction is detected without using the bright spot 20 or the like. Thus, it is possible to detect a line-of-sight direction in a wide range regardless of the irradiation position or the like of the bright spot 20. On the other hand, there is a possibility that a line-of-sight direction will not be accurately detected by this method if there is a positional shift of the eyeball 4 with respect to the camera.

In the HMD 100 according to the present embodiment, a first line-of-sight vector is calculated using the pupil-corneal reflex method, and a second line-of-sight vector is calculated using the pupil method. Then, a synthesis line-of-sight vector obtained by synthesizing the first line-of-sight vector and the second line-of-sight vector is calculated on the basis of information regarding the reliability of the first line-of-sight vector (the weighting coefficient $w_c$).

This makes it possible to dynamically mixedly use a line-of-sight detection using the pupil-corneal reflection method, and a line-of-sight detection using the pupil method with high environmental tolerance that does not depend on a reflection state or the like of the infrared light 15, the line-of-sight detection using the pupil-corneal reflection method being detection performed with a high degree of accuracy, the line-of-sight detection using the pupil method being detection that has a high environmental tolerance and does not depend on a reflection state or the like of the infrared light 15. In other words, it is possible to detect a line-of-sight direction by continuously synthesizing a first line-of-sight vector with a high degree of accuracy and a second line-of-sight vector covering a wide range. This makes it possible to stably detect a line of sight with a high degree of accuracy in a wide range.

For example, when the corneal region 8 is irradiated with the infrared light 15, a line-of-sight direction in which the proportion of a first line-of-sight vector is high is detected. Further, when the infrared light 15 is irradiated outside of the corneal region 8, a line-of-sight direction in which the proportion of a second line-of-sight vector is high is detected. As described above, in the present embodiment, it is possible to properly detect a line-of-sight direction of the user 1 according to the position of irradiation performed with the infrared light 15 (the position of the bright spot 20).

For this reason, for example, it is possible to detect a proper line of sight depending on the irradiation position of the bright spot 20 with respect to the user 1 of a different eye relief (such as the position of the eye in depth), and thus to reduce a difference in detection accuracy or the like due to an individual difference among the users 1. This makes it possible to improve the reliability of the apparatus and to provide a stable viewing experience and the like. Further, even when the user 1 uses glasses or the like, it is possible to properly detect a line-of-sight direction of the user 1. This makes it possible to sufficiently improve the usability of the apparatus.

For example, when switching between a result of detection performed using the pupil-corneal reflection method and a result of detection performed using the pupil method is performed at a specified timing to use one of the detection results, there is a possibility that a result of detecting a line of sight will be discontinuously changed and the detection result will not be stable. Conversely, in the present embodiment, a first line-of-sight vector and a second line-of-sight vector are synthesized using a weighting coefficient. This results in a reduction in an unnatural change or the like of the detection result, and it is possible to sufficiently stably detect a line-of-sight direction of the user 1. This makes it possible to, for example, improve the convenience for the user 1, and to exhibit an excellent operation performance.

In the present embodiment, the second correction parameter (the second calibration table) used for the pupil method is updated using the pupil-corneal reflection method used to perform a high-accuracy line-of-sight detection that makes it possible to successfully deal with a positional shift the eyeball. This makes it possible to correct a second correction parameter with a high degree of accuracy, and to maintain, for example, the accuracy in detecting a second line-of-sight vector at a high level.

As described above, even when there is a positional shift of the eyeball 4, for example, due to attachment of the HMD 100 being loosened, or due to the movement of the user 1, it is possible to calculate a second line-of-sight vector with a high degree of accuracy by automatically updating the second correction parameter. This results in being able to sufficiently stably detect a line of sight, and to greatly improve the reliability of the apparatus. Consequently, there is an improvement in a performance to cope with the movement of the user 1, and this enables the user 1 to fully enjoy a game and the like in a VR space using the HMD 100.

Second Embodiment

An HMD according to a second embodiment of the present technology is described. In the following description, descriptions of a configuration and an operation similar to those of the HMD 100 described in the embodiment above are omitted or simplified.

In the present embodiment, as processing of calculating a line-of-sight direction using the pupil-corneal reflection method, a line-of-sight direction is calculated using two different methods. Specifically, a method of calculating a line-of-sight direction using a pair of bright spots 20, and a method of calculating a line-of-sight direction using a single bright spot 20 are used.

For example, a method of estimating a line-of-sight direction using the eyeball model 50 described with reference to, for example, FIG. 11 is used as the method of using the pair of bright spots 20. In other words, a method is used that includes estimating the optical axis 53 of the eyeball model 50 on the basis of the position of the bright spot 20, and calculating the visual axis 55 (a line-of-sight vector) from the estimated optical axis 53. The line-of-sight vector calculated using a pair of bright spots 20 is hereinafter referred to as a third line-of-sight vector. In the present embodiment, the method of estimating a line-of-sight direction using a pair of bright spots 20 corresponds to the first method, and the third line-of-sight vector corresponds to the first line-of-sight direction.

For example, a method of estimating a line-of-sight direction by calculating a relative position of the bright spot 20 with respect to the pupil 5 is used as the method of using a single bright spot 20. For example, a relative position of the bright spot 20 with respect to the pupil center 22 in a state in which a marker is being gazed at, is detected by performing the calibration processing. The detected relative position is recorded in a calibration table in association with a line-of-sight vector (a line-of-sight vector for correction) that is oriented toward the marker.

For example, by referring to a relative position recorded in a calibration table as appropriate, it is possible to calculate a line-of-sight vector of a user in the eyeball image 21 from a relative position of the bright spot 20 with respect to the pupil center 22 in the eyeball image 21 to be calculated. The line-of-sight vector calculated using a single bright spot 20 is hereinafter described as a fourth line-of-sight vector. In the present embodiment, the method of estimating a line-of-sight direction using a single bright spot 20 corresponds to the second method, and the fourth line-of-sight vector corresponds to the second line-of-sight direction.

In the present embodiment, the third line-of-sight vector calculated using a pair of bright spots 20 and the fourth line-of-sight vector calculated using a single bright spot 20 are synthesized to calculate a synthesis line-of-sight vector. The third line-of-sight vector and the fourth line-of-sight vector are synthesized on the basis of a specified synthesis ratio. A specific description is made below.

Figure 16A:
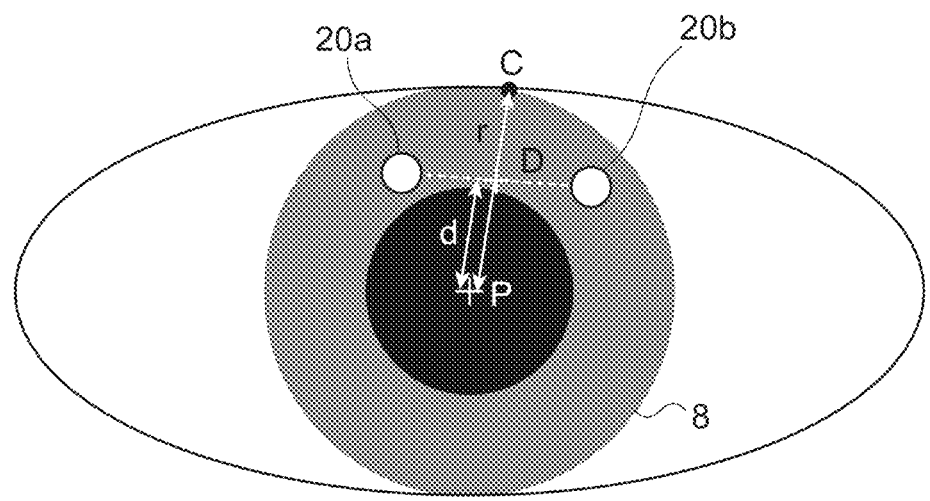
FIGS. 16A and 16B are schematic diagrams for describing an example of processing of calculating a synthesis ratio used to synthesize third and fourth line-of-sight vectors.
Figure 16B:
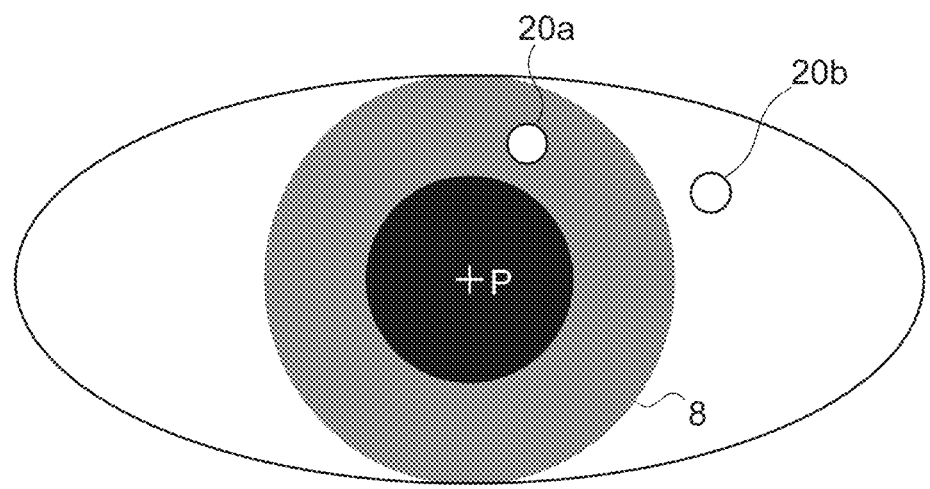

FIGS. 16A and 16B are schematic diagrams for describing an example of processing of calculating a synthesis ratio used to synthesize the third and fourth line-of-sight vectors. In FIG. 16A, a first bright spot 20a and a second bright spot 20b are included in the corneal region 8.

For example, the third line-of-sight vector is calculated on the basis of a pair of the first bright spot 20a and the second bright spot 20b by a method using a pair of bright spots 20. The fourth line-of-sight vector is calculated using only the first bright spot 20a (or the second bright spot 20a) by using a single bright spot 20. Alternatively, the fourth line-of-sight vector may be calculated by synthesizing a line-of-sight vector calculated from the first bright spot 20a and a line-of-sight vector calculated from the second bright spot 20a.

With respect to the processing of calculating the third and fourth line-of-sight vectors, for example, the calculations are performed in parallel. The calculated third and fourth line-of-sight vectors are appropriately synthesized on the basis of the weighting coefficient $w_c$ (a synthesis ratio). For example, on the basis of a pair of the first bright spot 20a and the second bright spot 20b, the weighting coefficient $w_c$ is calculated using Formula (1).

For example, as illustrated in FIG. 16B, when one of the pair (the second bright spot 20b) is situated outside of the corneal region 8, the weighting coefficient wc of the third line-of-sight vector is zero, and the weighting coefficient (1-wc) of the fourth line-of-sight vector is 1. Even in such a case, it is possible to seamlessly switch a synthesis line-of-sight vector from the fourth line-of-sight vector to the third line-of-sight vector, and thus to sufficiently avoid a state in which a result of detecting a line of sight is discontinuously changed.

Third Embodiment

In the present embodiment, different methods are used as a method of calculating a line-of-sight direction by extracting a feature of the eyeball 4 (an image feature) without using the bright spot 20. Specifically, a method of calculating a line-of-sight direction using position information regarding the position of a feature of the eyeball 4 and a method of calculating a line-of-sight direction using shape information regarding the shape of a feature of the eyeball 4 are used. Note that examples of the feature of the eyeball 4 include the pupil 5, the cornea 7, and the iris 6 of the eyeball 4.

Examples of the method using position information regarding the position of a feature of the eyeball 4 include a method including detecting a center position of the pupil 5, the cornea 7, or the like, and calculating a line-of-sight vector from the detected position on the basis of a specified calibration table. For example, the pupil method described in the first embodiment is an example of the method of calculating a line-of-sight direction using position information.

Further, for example, a line-of-sight recognition method using the positions of the pupil and the iris (corneal region 8) may be used. A line-of-sight vector calculated using position information regarding the position of a feature of the eyeball 4 is hereinafter referred to as a fifth line-of-sight vector. In the present embodiment, a method of estimating a line-of-sight direction using positional information regarding the position of a feature of the eyeball 4 corresponds to the first method, and the fifth line-of-sight vector corresponds to the first line-of-sight direction.

Examples of the method using shape information regarding the shape of a feature of the eyeball 4 include a method of extracting the shape of the pupil 5, the cornea 7, or the like, and calculating a line-of-sight direction from the shape. For example, it is possible to fit an elliptical shape to the pupil 5, the cornea 7, or the like, and to estimate a line-of-sight direction on the basis of the ellipticity or the like.

The line-of-sight vector calculated using shape information regarding the shape of a feature of the eyeball 4 is hereinafter referred to as a sixth line-of-sight vector. In the present embodiment, the method of estimating a line-of-sight direction using shape information regarding the shape of a feature of the eyeball 4 corresponds to the second method, and the sixth line-of-sight vector corresponds to the second line-of-sight direction.

Figure 17A:
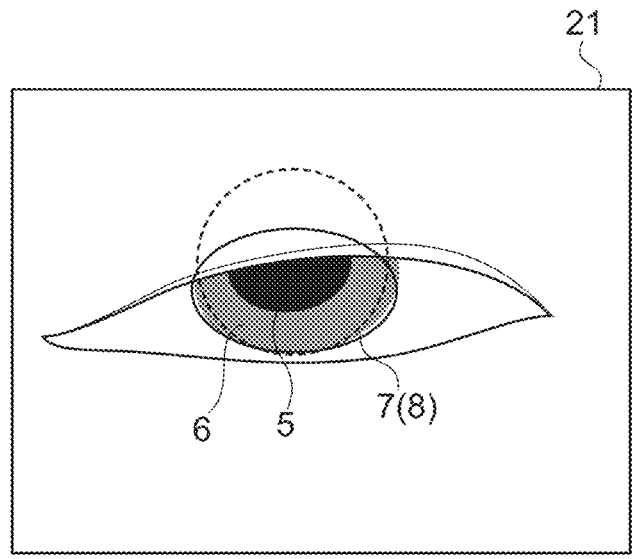
FIGS. 17A and 17B are schematic diagrams for describing a relationship between a line-of-sight direction of the user and a feature.
Figure 17B:
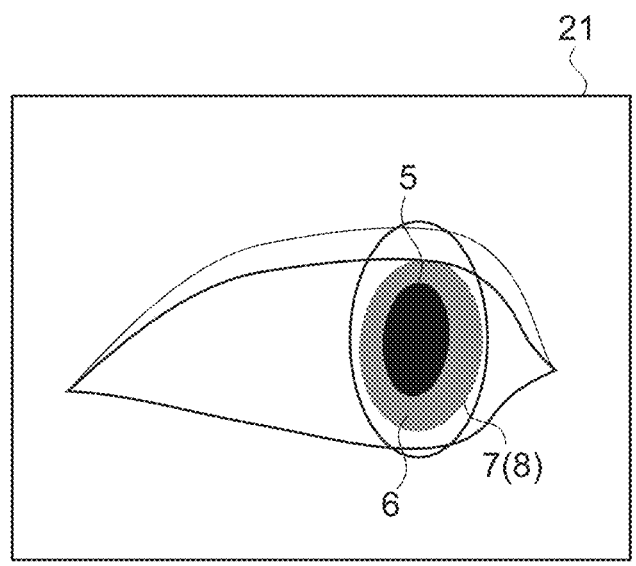

FIGS. 17A and 17B are schematic diagrams for describing a relationship between a line-of-sight direction of the user 1 and a feature. The case of detecting the corneal region 8 as a feature of the eyeball 4 is described below as an example. FIG. 17A schematically illustrates the eyeball image 21 when a portion of the corneal region 8 is hidden under an upper eyelid of the user 1. FIG. 17B schematically illustrates the eyeball image 21 when the user 1 is looking at a surrounding portion of the eye region 3.

As illustrated in FIG. 16A, when, for example, the corneal region 8 (a non-white part of the eyeball) of the user 1 is hidden under the eyelid, it may be difficult to properly detect the shape of the corneal region 8. For example, when an elliptical shape is fit to the corneal region 8 hidden in the eyelid, there is a possibility that, even when the user 1 is looking to the front, fitting will be performed with, for example, a horizontally long ellipse (in a solid line in the figure), compared to an actual corneal shape (in a dotted line in the figure).

On the other hand, when the user 1 is looking to the front in a state in which the corneal region 8 is not hidden under the eyelid, the corneal region 8 is a substantially perfect circle. In this case, there will not be a great change in the ellipticity or the like of the elliptical shape fitted to the corneal region 8 even if the line of sight is moved. Thus, for example, it may be difficult to obtain a detailed elliptical shape in a central portion of the eye region 3. Note that, in the central portion of the eye region 3, the calculation of a center position or the like of an elliptical shape makes it possible to calculate a line-of-sight direction with a high degree of accuracy.

Further, when the user 1 is looking to the left and right and when the corneal region 8 (the pupil 5) is situated in the surrounding portion of the eye region 3, as illustrated in FIG. 16B, the corneal region 8 has a vertically long elliptical shape due to the spherical eyeball 4 being rotated. In this case, the elliptical shape is greatly changed due to a change in a line of sight of the user 1, and there is also an increase in an amount of change in ellipticity. Thus, in the surrounding portion of the eye region 3, it is possible to calculate a line-of-sight direction of the user 1 with a high degree of accuracy by referring to an elliptical shape fitted to the corneal region 8. Note that, in the surrounding portion of the eye region 3, the amount of change or the like in the center position of the corneal region 8 is smaller than that in the central portion.

In the processing of synthesizing the fifth line-of-sight vector and the sixth line-of-sight vector, the weighting coefficient of each line-of-sight vector is set on the basis of the ellipticity or the like of an elliptical shape. For example, it is possible to set a weighting coefficient as appropriate such that the weighting coefficient of the fifth line-of-sight vector calculated using position information is higher if the shape of the corneal region 8 (an elliptical shape to be fitted) is changed from a perfect circle to be horizontally longer, and such that the weighting coefficient of the sixth line-of-sight vector calculated using shape information is higher if the elliptical shape is vertically longer.

This makes it possible to calculate a synthesis line-of-sight vector in which the proportion of the fifth line-of-sight vector obtained using position information is high in the central portion of the eye region 3 and the proportion of the sixth line-of-sight vector obtained using shape information is high in the surrounding portion of the eye region 3. This results in being able to calculate a line-of-sight vector with a high degree of accuracy in both the central portion and the surrounding portion. Further, it is possible to stably detect a line of sight without a discontinuous change or the like since switching is smoothly performed between the fifth and sixth line-of-sight vectors.

Other Embodiments

The present technology is not limited to the embodiments described above, and can achieve various other embodiments.

In the processing illustrated in FIG. 10, the second correction parameter used to calculate the second line-of-sight vector is updated using a weighting coefficient used to synthesize the first line-of-sight vector and the second line-of-sight vector. The update processing is not limited to this, and any processing performed to update the second correction parameter may be used.

For example, it may be determined whether the first line-of-sight vector has been calculated, and the second correction parameter may be updated on the basis of a result of the determination. In other words, processing of updating the second correction parameter when the first line-of-sight vector is detected using the pupil-corneal reflection method, may be performed. Further, for example, the reliability of the first line-of-sight vector and the reliability of the second line-of-sight vector may be compared, and the second correction parameter may be updated on the basis of a result of the comparison. In other words, processing of not updating the second correction parameter when the reliability of the second line-of-sight vector is sufficiently high, may be performed.

Further, on the basis of the second line-of-sight vector, the first correction parameter (the first calibration table) used to calculate the first line-of-sight vector may be updated. For example, processing of updating the first calibration table on the basis of the second line-of-sight vector when, for example, the reliability of the second line-of-sight vector is sufficiently high and there is a reduction in the reliability of the first line-of-sight vector, may be performed.

In the processing illustrated in FIG. 10, a line-of-sight direction of the user 1 is determined by synthesizing the first line-of-sight vector and the second line-of-sight vector. The determination processing is not limited to this, and processing of determining a line-of-sight direction of the user 1 by selecting one of the first line-of-sight vector and the second line-of-sight vector, may be performed.

For example, determination processing that includes calculating the reliability of the first line-of-sight vector and the reliability of the second line-of-sight, and determining a line-of-sight vector having a higher reliability to be a line-of-sight direction of the user, may be performed. This makes it possible to easily determine a line-of-sight direction of the user, and to reduce a processing time, a calculation amount, and the like.

Further, processing of updating the second correction parameter and the like may be performed together with processing of determining the first and second line-of-sight vectors. For example, the second correction parameter is updated using the first line-of-sight vector when the first line-of-sight vector is greater than a specified threshold. Such processing may be performed. This makes it possible to calculate the second line-of-sight vector with a high degree of accuracy even when a relative position of the eyeball with respect to the camera is shifted, for example, due to the movement of the user, or due to the HMD or the like being loosened.

Further, it is possible to sufficiently avoid a state in which a result of detecting a line of sight is discontinuously changed when switching between the first line-of-sight vector and the second line-of-sight vector is performed. This makes it possible to perform a stable line-of-sight detection that makes it possible to successfully deal with a positional shift.

In the example illustrated in FIG. 12A, the weighting coefficient of the first line-of-sight vector is calculated using a pair of bright spots 20. The calculation is not limited to this, and it is also possible to calculate the weighting coefficient when a single bright spot 20 is used. For example, by replacing the midpoint D1 of the pair of bright spots 20 illustrated in FIG. 12A with a center position of a single bright spot 20, it is possible to calculate the weighting coefficient related to the first line-of-sight vector that is calculated using the single bright spot 20. This also makes it possible to properly synthesize the first line-of-sight vector and the second line-of-sight vector when it is not possible to detect a pair of bright spots 20.

Figure 18:
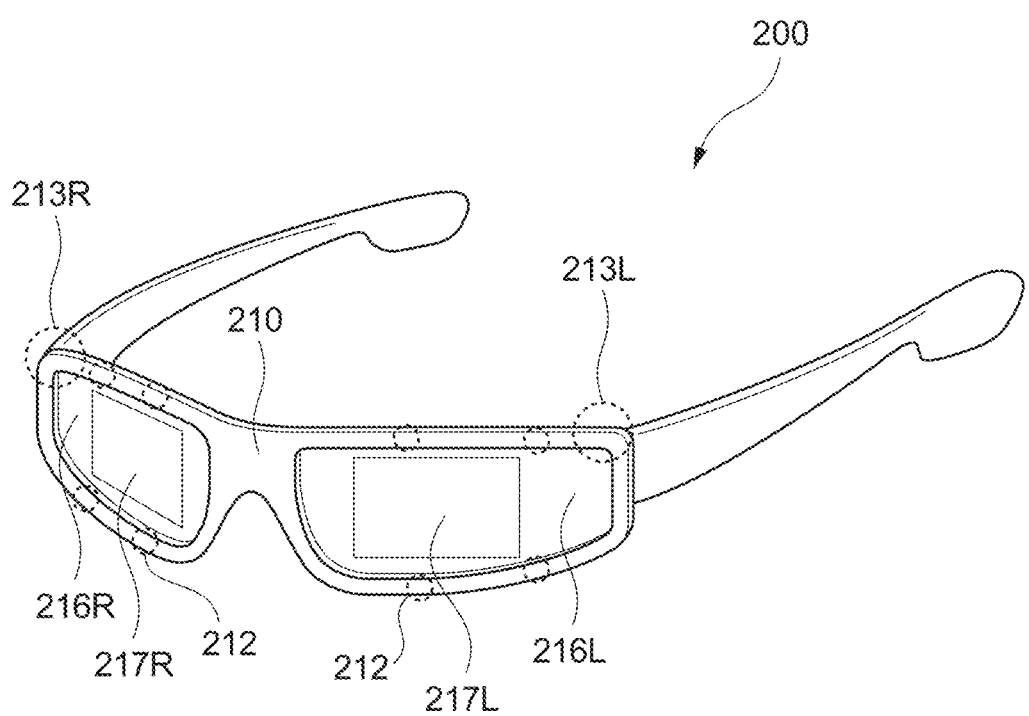
FIG. 18 is a perspective view illustrating an appearance of an HMD according to another embodiment.

FIG. 18 is a perspective view illustrating an appearance of an HMD according to another embodiment. An HMD 200 is an eyeglass-style apparatus including a transmissive display, and is used by being worn on the head of a user.

The HMD 200 includes a frame 210, a plurality of infrared light sources 212, left and right infrared cameras 213L and 213R, left and right lens 216L and 216R, and left and right transmissive displays 217L and 217R. Further, a controller or the like substantially similar to that illustrated in FIG. 5 is in the frame 210 or at a specified position of the frame 210.

Infrared light sources 212 of the plurality of infrared light sources 212 are each arranged at a specified position of the frame 210 such that the infrared light sources 212 are each capable of irradiating infrared light onto the eyeball of the user 1. In FIGS. 12A and 12B, four infrared light sources 212 that each irradiate infrared light onto the right eye of the user, and four infrared light sources 212 that each irradiate infrared light onto the left eye of the user are respectively provided. The number of infrared light sources 212 and the arrangement of the infrared light source 212 are not limited, and, for example, they may be set according to, for example, an image-capturing range of the infrared camera 213.

The left and right infrared cameras 213L and 213R are respectively arranged at specified positions of the frame such that the left and right infrared cameras 213L and 213R are respectively capable of capturing an image of the left eye of the user and an image of the right eye of the user. For example, an infrared image of the left eye and an infrared image of the right eye that are captured by the infrared cameras 213L and 213R are used as eyeball images of the user 1.

The left and right lens 216L and 216R are respectively arranged in front of the left and right eyes of the user. The transmissive displays 217L and 217R are respectively provided on the left and right lens 216L and 216R to cover the field of view of the user.

The transmissive displays 217L and 217R are transmissive displays, and images and the like for the left eye and the right eye are respectively displayed on the transmissive displays 217L and 217R. The user who is wearing the HMD 200 can visually confirm an actual scenery and visually confirm images displayed on the respective displays at the same time. This enables the user to experience an augmented reality (AR) or the like.

Note that each transmission display may include a light control element or the like that blocks light from the outside. This enables the user to perform visual confirmation in which an actual scenery visually confirmed by the user is controlled and images displayed on the displays are emphasized. This enables the user to experience a virtual reality (VR) or the like.

For example, an eyeball image is captured in a state in which pieces of infrared light are irradiated onto the eyeball of the user by a plurality of infrared light sources 212. Using the captured eyeball image, line-of-sight vectors are respectively calculated by the pupil-corneal reflection method and by the pupil method. A synthesis line-of-sight vector obtained by synthesizing the respective line-of-sight vectors on the basis of a specified weighting coefficient is calculated as a line-of-sight direction of the user. This makes it possible to stably detect a line-of-sight direction of the user.

As described above, the present technology is also applicable to a transmissive HMD such as AR glasses. For example, an image display or the like is performed according to a line-of-sight direction of the user when AR experience is provided. For example, it is possible to stably display content or the like with a high degree of accuracy using a line-of-sight result or the like calculated using the present technology.

In the embodiments above, infrared light is irradiated onto the central region of the eye region of the user. The irradiation of infrared light is not limited to this, and the infrared light may be irradiated onto a surrounding region of the eye region. For example, in the case of a transmission HMD as illustrated in FIG. 18, it may be difficult to provide an infrared camera or the like at a position at which it is possible to capture an image of the eye of a user from the front. In such a case, the infrared camera is arranged to capture an image of the eye of the user at an angle.

For example, the infrared light source is arranged such that infrared light is irradiated onto the surrounding region of the eye region of the user according to an image-capturing range of the infrared camera. This makes it possible to use the pupil-corneal reflection method even when the pupil of the user is away from the front, and to calculate a line-of-sight direction of the user with a high degree of accuracy.

When the user is looking to the front, it is possible to calculate a line-of-sight direction of the user using the pupil method. In other words, the line-of-sight direction is calculated using the pupil method in a center portion of the field of view of the user, and the line-of-sight direction is calculated using the pupil-corneal reflection method in a surrounding portion of the field of view of the user. Such a configuration may be adopted.

Even in the case of such a configuration, it is possible to update a calibration table or the like used in the pupil method, using a line-of-sight direction that is calculated using the pupil-corneal reflection method. This makes it possible to perform a stable line-of-sight detection that makes it possible to successfully deal with a positional shift of the eyeball even in the case of an eyeglass-style HMD or the like.

In the embodiments above, an eyewear apparatus such as an HMD has been primarily described. The present technology is not limited to this, and is applicable to any apparatus that detects a line of sight. For example, the present technology may be applied to a case of detecting a line of sight using, for example, an in-car driver monitoring apparatus that detects a line of sight using a camera installed in a vehicle or the like, a line-of-sight operation UI apparatus for medical use that is used for a technical expert, or a Web camera. For example, it is possible to stably detect a line of sight by synthesizing line-of-sight vectors respectively detected by different detection methods. Moreover, the present technology is applicable in medical practice, or in various fields such as entertainment and marketing.

In the description above, the information processing method according to the present technology including, for example, determining a line-of-sight direction of a user, is performed by the controller. The present technology is not limited to this, and a cloud server may perform the information processing method according to the present technology. In other words, a function of the controller may be included in a cloud server. In this case, the cloud server operates as the information processing apparatus according to the present technology.

Further, the information processing method and the program according to the present technology may be performed and the information processing apparatus according to the present technology may be implemented by a computer included in the HMD (the controller) and another computer (a cloud server) that is capable of communicating with the computer via a network or the like working cooperatively.

In other words, the information processing method and the program according to the present technology can be performed not only in a computer system formed of a single computer, but also in a computer system in which a plurality of computers operates cooperatively. Note that, in the present disclosure, the system refers to a set of components (such as apparatuses and modules (parts)) and it does not matter whether all of the components are in a single housing. Thus, a plurality of apparatuses accommodated in separate housings and connected to one another via a network, and a single apparatus in which a plurality of modules is accommodated in a single housing are both the system.

The execution of the information processing method and the program according to the present technology by the computer system includes, for example, both a case in which the acquisition of eye information regarding an eye of a user, the determination of a first line-of-sight direction, the determination of a second line-of-sight direction, the calculation of reliability information, and the determination of a line-of-sight direction of a user are executed by a single computer; and a case in which the respective processes are executed by different computers. Further, the execution of each process by a specified computer includes causing another computer to execute a portion of or all of the process and acquiring a result of it.

In other words, the information processing method and the program according to the present technology are also applicable to a configuration of cloud computing in which a single function is shared and cooperatively processed by a plurality of apparatuses via a network.

At least two of the features of the present technology described above can also be combined. In other words, the various features described in the respective embodiments may be combined discretionarily regardless of the embodiments. Further, the various effects described above are not limitative but are merely illustrative, and other effects may be provided.

Note that the present technology may also take the following configurations.

(1) An information processing apparatus, including:
an acquisition section that acquires eye information regarding an eye of a user; and
a processor that
determines a first line-of-sight direction on the basis of the eye information using a first method,
determines a second line-of-sight direction on the basis of the eye information using a second method that is different from the first method,
calculates reliability information regarding at least one of reliability of the first line-of-sight direction or reliability of the second line-of-sight direction, and
determines a line-of-sight direction of the user on the basis of the calculated reliability information.

(2) The information processing apparatus according to (1), in which
on the basis of the reliability information, the processor synthesizes the first line-of-sight direction and the second line-of-sight direction, and determines the line-of-sight direction of the user.

(3) The information processing apparatus according to (2), in which
the reliability information includes a weighting coefficient used to synthesize the first line-of-sight direction and the second line-of-sight direction.

(4) The information processing apparatus according to (3), in which
the eye information includes an eyeball image of an eyeball of the user, the eyeball image being obtained by performing image-capturing on the eyeball in a state of being irradiated with at least one piece of irradiation light, and
the first method is a method including detecting, from the eyeball image, at least one bright spot generated due to the at least one piece of irradiation light, and determining the first line-of-sight direction on the basis of the detected at least one bright spot.

(5) The information processing apparatus according to (4), in which
the at least one piece of irradiation light is a plurality of pieces of irradiation light, and
the processor is capable of detecting, from the eyeball image, a pair of bright spots from among a plurality of bright spots generated due to the plurality of pieces of irradiation light, the pair of bright spots being a pair of bright spots provided in a specified arrangement.

(6) The information processing apparatus according to (5), in which
the processor detects a corneal region of the eyeball, and calculates the weighting coefficient on the basis of a position of the pair of bright spots in the corneal region.

(7) The information processing apparatus according to (5) or (6), in which
the processor detects a pupil center of the eyeball, and calculates the weighting coefficient on the basis of a distance from the pair of bright spots to the pupil center.

(8) The information processing apparatus according to any one of (5) to (7), in which
the processor calculates an area of the bright spot, and calculates the weighting coefficient on the basis of the calculated area of the bright spot.

(9) The information processing apparatus according to any one of (5) to (8), in which
the first method is a method of determining the first line-of-sight direction on the basis of the pair of bright spots from among the plurality of bright spots, and
the second method is a method of determining the second line-of-sight direction on the basis of a single bright spot from among the plurality of bright spots.

(10) The information processing apparatus according to any one of (1) to (9), in which
the processor updates at least one of a first correction parameter or a second correction parameter on the basis of the reliability information, the first correction parameter being used to determine the first line-of-sight direction, the second correction parameter being used to determine the second line-of-sight direction.

(11) The information processing apparatus according to (10), in which
the first method is a method of determining the first line-of-sight direction on the basis of a reference point that is set on a surface of the eyeball, and
the processor updates the second correction parameter on the basis of the first line-of-sight direction.

(12) The information processing apparatus according to (10) or (11), in which
the reliability information includes reliability of the first line-of-sight direction, and
the processor updates the second correction parameter according to the reliability of the first line-of-sight direction.

(13) The information processing apparatus according to (12), in which
the eye information includes an eyeball image of an eyeball of the user, the eyeball image being obtained by performing image-capturing on the eyeball in a state of being irradiated with at least one piece of irradiation light,
the first method is a method including detecting, from the eyeball image, at least one bright spot generated due to the at least one piece of irradiation light, and determining the first line-of-sight direction on the basis of the detected at least one bright spot, and
the processor calculates the reliability of the first line-of-sight direction on the basis of the eyeball image.

(14) The information processing apparatus according to (13), in which
the at least one piece of irradiation light is irradiated onto one of a central region or a surrounding region of the eye region.

(15) The information processing apparatus according to any one of (10) to (14), in which
the processor updates the second correction parameter according to a position of a pupil in an eye region in the eyeball image, the eye region including the eyeball.

(16) The information processing apparatus according to any one of (10) to (15), in which
the reliability information includes a weighting coefficient used to synthesize the first line-of-sight direction and the second line-of-sight direction, and
the processor corrects the second correction parameter on the basis of the weighting coefficient.

(17) The information processing apparatus according to any one of (1) to (16), in which
the second method is a method of determining the second line-of-sight direction by detecting at least one of a position or a shape of a specified feature of the eyeball from the eyeball image.

(18) The information processing apparatus according to (17), in which
the specified feature includes one of a pupil, a cornea, and an iris of the eyeball.

(19) An information processing method, including:
acquiring, by a computer system, eye information regarding an eye of a user;
determining, by the computer system, a first line-of-sight direction on the basis of the eye information using a first method;
determining, by the computer system, a second line-of-sight direction on the basis of the eye information using a second method that is different from the first method;
calculating, by the computer system, reliability information regarding at least one of reliability of the first line-of-sight direction or reliability of the second line-of-sight direction; and
determining, by the computer system, a line-of-sight direction of the user on the basis of the calculated reliability information.

(20) A program that causes a computer system to perform a process including:
acquiring eye information regarding an eye of a user;
determining a first line-of-sight direction on the basis of the eye information using a first method;
determining a second line-of-sight direction on the basis of the eye information using a second method that is different from the first method;
calculating reliability information regarding at least one of reliability of the first line-of-sight direction or reliability of the second line-of-sight direction; and
determining a line-of-sight direction of the user on the basis of the calculated reliability information.

REFERENCE SIGNS LIST $E_c$ first line-of-sight vector
$E_i$ second line-of-sight vector
E synthesis line-of-sight vector
$w_c$ weighting coefficient
1 user
3 eye region
8 corneal region
12, 12a to 12d, 212 infrared light source 13, 13L, 13R, 213L, 213R infrared camera
15 infrared light
20, 20a, 20b bright spot
21, 21a, 21b eyeball image
22 pupil center
30 controller
31 image acquisition section
32 image processor
33 first line-of-sight detector
34 second line-of-sight detector
35 synthesis ratio calculator
36 line-of-sight synthesis section
37 correction parameter update section
40 corneal region detector
41 bright spot detector
42 pupil center detector
100, 200 HMD

The invention claimed is:

1. An information processing apparatus, comprising:
a central processing unit (CPU) configured to:
   acquire eye information regarding an eye of a user; and
   determine a first line-of-sight direction based on the eye information using a first method, wherein
      the eye information includes an eyeball image of an eyeball of the user,
      the eyeball image is obtained by performing image-capturing on the eyeball in a state of being irradiated with at least one piece of irradiation light,
      the at least one piece of irradiation light is a plurality of pieces of irradiation light,
      the first method is a method including detecting, from the eyeball image, at least one bright spot generated due to the at least one piece of irradiation light, and determining the first line-of-sight direction based on the detected at least one bright spot;
   determine a second line-of-sight direction based on the eye information using a second method that is different from the first method;
   calculate reliability information regarding at least one of reliability of the first line-of-sight direction or reliability of the second line-of-sight direction;
   synthesize, based on the reliability information, the first line-of-sight direction and the second line-of-sight direction, wherein
      the reliability information includes a weighting coefficient used to synthesize the first line-of-sight direction and the second line-of-sight direction;
   determine a line-of-sight direction of the user, based on the synthesized first line-of-sight direction and the synthesized second line-of-sight direction;
   detect, from the eyeball image, a pair of bright spots from among a plurality of bright spots generated due to the plurality of pieces of irradiation light, wherein
      the pair of bright spots is a pair of bright spots provided in a specified arrangement;
   detect a corneal region of the eyeball; and
   calculate the weighting coefficient based on a position of the pair of bright spots in the corneal region.

2. The information processing apparatus according to claim 1, wherein the CPU is further configured to:
   detect a pupil center of the eyeball, and
   calculate the weighting coefficient based on a distance from the pair of bright spots to the pupil center.

3. The information processing apparatus according to claim 1, wherein the CPU is further configured to:
   calculate an area of the at least one bright spot, and
   calculate the weighting coefficient based on the calculated area of the at least one bright spot.

4. The information processing apparatus according to claim 1, wherein
   the first method is a method of determining the first line-of-sight direction based on the pair of bright spots from among the plurality of bright spots, and
   the second method is a method of determining the second line-of-sight direction based on a single bright spot from among the plurality of bright spots.

5. The information processing apparatus according to claim 1, wherein the CPU is further configured to
   update at least one of a first correction parameter or a second correction parameter based on the reliability information, the first correction parameter being used to determine the first line-of-sight direction, the second correction parameter being used to determine the second line-of-sight direction.

6. The information processing apparatus according to claim 5, wherein
   the first method is a method of determining the first line-of-sight direction based on a reference point that is set on a surface of the eyeball, and
   the CPU is further configured to update the second correction parameter based on the first line-of-sight direction.

7. The information processing apparatus according to claim 5, wherein
   CPU is further configured to update the second correction parameter according to the reliability of the first line-of-sight direction.

8. The information processing apparatus according to claim 7, wherein
   CPU is further configured to calculate the reliability of the first line-of-sight direction based on the eyeball image.

9. The information processing apparatus according to claim 8, wherein the at least one piece of irradiation light is irradiated onto one of a central region or a surrounding region of an eye region of the user.

10. The information processing apparatus according to claim 5, wherein the CPU is further configured to
    update the second correction parameter based on a position of a pupil in an eye region in the eyeball image, the eye region including the eyeball.

11. The information processing apparatus according to claim 5, wherein
    the CPU is further configured to correct the second correction parameter based on the weighting coefficient.

12. The information processing apparatus according to claim 1, wherein
    the second method is a method of determining the second line-of-sight direction by detecting at least one of a position or a shape of a specified feature of the eyeball from the eyeball image.

13. The information processing apparatus according to claim 12, wherein the specified feature includes one of a pupil, a cornea, or an iris of the eyeball.

14. An information processing method, comprising:
    acquiring, by a computer system, eye information regarding an eye of a user;
    determining, by the computer system, a first line-of-sight direction based on the eye information using a first method, wherein
       the eye information includes an eyeball image of an eyeball of the user, the eyeball image is obtained by performing image-capturing on the eyeball in a state of being irradiated with at least one piece of irradiation light, the at least one piece of irradiation light is a plurality of pieces of irradiation light, the first method is a method including detecting, from the eyeball image, at least one bright spot generated due to the at least one piece of irradiation light, and determining the first line-of-sight direction based on the detected at least one bright spot;

determining, by the computer system, a second line-of-sight direction based on the eye information using a second method that is different from the first method;

calculating, by the computer system, reliability information regarding at least one of reliability of the first line-of-sight direction or reliability of the second line-of-sight direction;

synthesizing, based on the reliability information, the first line-of-sight direction and the second line-of-sight direction, wherein the reliability information includes a weighting coefficient used to synthesize the first line-of-sight direction and the second line-of-sight direction;

determining, by the computer system, a line-of-sight direction of the user, based on the synthesized first line-of-sight direction and the synthesized second line-of-sight direction;

detecting, from the eyeball image, a pair of bright spots from among a plurality of bright spots generated due to the plurality of pieces of irradiation light, wherein the pair of bright spots is a pair of bright spots provided in a specified arrangement;

detecting a corneal region of the eyeball; and calculating the weighting coefficient based on a position of the pair of bright spots in the corneal region.

15. A non-transitory computer-readable medium having stored thereon computer-executable instructions which, when executed by a computer, cause the computer to execute operations, the operations comprising:

acquiring eye information regarding an eye of a user;

determining a first line-of-sight direction based on the eye information using a first method, wherein the eye information includes an eyeball image of an eyeball of the user, the eyeball image is obtained by performing image-capturing on the eyeball in a state of being irradiated with at least one piece of irradiation light, the at least one piece of irradiation light is a plurality of pieces of irradiation light, the first method is a method including detecting, from the eyeball image, at least one bright spot generated due to the at least one piece of irradiation light, and determining the first line-of-sight direction based on the detected at least one bright spot;

determining a second line-of-sight direction based on the eye information using a second method that is different from the first method;

calculating reliability information regarding at least one of reliability of the first line-of-sight direction or reliability of the second line-of-sight direction;

synthesizing, based on the reliability information, the first line-of-sight direction and the second line-of-sight direction, wherein the reliability information includes a weighting coefficient used to synthesize the first line-of-sight direction and the second line-of-sight direction;

determining a line-of-sight direction of the user, based on the synthesized first line-of-sight direction and the synthesized second line-of-sight direction;

detecting, from the eyeball image, a pair of bright spots from among a plurality of bright spots generated due to the plurality of pieces of irradiation light, wherein the pair of bright spots is a pair of bright spots provided in a specified arrangement;

detecting a corneal region of the eyeball; and calculating the weighting coefficient based on a position of the pair of bright spots in the corneal region.

\* \* \* \* \*